(12) United States Patent
Majuru et al.

(10) Patent No.: US 9,364,502 B2
(45) Date of Patent: Jun. 14, 2016

(54) GALLIUM NITRATE FORMULATIONS

(75) Inventors: Shingai Majuru, Brewster, NY (US); Moses O. Oyewumi, Yorktown Heights, NY (US); Mehmet Tahir Gurler, Oakland Gardens, NY (US)

(73) Assignee: EMISPHERE TECHNOLOGIES, INC., Roseland, NJ (US)

( * ) Notice: Subject to any disclaimer, the term of this patent is extended or adjusted under 35 U.S.C. 154(b) by 167 days.

(21) Appl. No.: 12/305,907

(22) PCT Filed: Jun. 28, 2007

(86) PCT No.: PCT/US2007/072373
§ 371 (c)(1),
(2), (4) Date: Dec. 19, 2008

(87) PCT Pub. No.: WO2008/003050
PCT Pub. Date: Jan. 3, 2008

(65) Prior Publication Data
US 2010/0239658 A1  Sep. 23, 2010

Related U.S. Application Data

(60) Provisional application No. 60/817,561, filed on Jun. 28, 2006, provisional application No. 60/881,044, filed on Jan. 17, 2007.

(51) Int. Cl.
*A61K 9/48* (2006.01)
*A61K 33/24* (2006.01)
*A61K 9/00* (2006.01)

(52) U.S. Cl.
CPC .. *A61K 33/24* (2013.01); *A61K 9/00* (2013.01)

(58) Field of Classification Search
None
See application file for complete search history.

(56) References Cited

U.S. PATENT DOCUMENTS

| | | | |
|---|---|---|---|
| 4,529,593 A | 7/1985 | Warrell, Jr. et al. | |
| 4,704,277 A | 11/1987 | Bockman et al. | |
| 5,196,412 A | 3/1993 | Bradley et al. | |
| 5,258,376 A | 11/1993 | Bernstein | |
| 5,401,516 A | 3/1995 | Milstein et al. | |
| 5,443,841 A | 8/1995 | Milstein et al. | |
| 5,447,728 A | 9/1995 | Milstein et al. | |
| 5,451,410 A | 9/1995 | Milstein et al. | |
| 5,525,598 A | 6/1996 | Collery et al. | |
| 5,540,939 A | 7/1996 | Milstein et al. | |
| 5,541,155 A | 7/1996 | Leone-Bay et al. | |
| 5,556,645 A | 9/1996 | Bockman et al. | |
| 5,574,027 A | 11/1996 | Bernstein | |
| 5,578,323 A | 11/1996 | Milstein et al. | |
| 5,601,846 A | 2/1997 | Milstein et al. | |
| 5,629,020 A | 5/1997 | Leone-Bay et al. | |
| 5,643,957 A | 7/1997 | Leone-Bay et al. | |
| 5,650,386 A | 7/1997 | Leone-Bay et al. | |
| 5,667,806 A | 9/1997 | Kantor | |
| 5,686,116 A | 11/1997 | Bockman et al. | |
| 5,693,338 A | 12/1997 | Milstein | |
| 5,709,861 A | 1/1998 | Santiago et al. | |
| 5,714,167 A | 2/1998 | Milstein et al. | |
| 5,750,147 A | 5/1998 | Kantor | |
| 5,766,633 A | 6/1998 | Milstein et al. | |
| 5,773,647 A | 6/1998 | Leone-Bay et al. | |
| 5,776,888 A | 7/1998 | Leone-Bay et al. | |
| 5,792,451 A | 8/1998 | Sarubbi et al. | |
| 5,804,688 A | 9/1998 | Leone-Bay et al. | |
| 5,811,127 A | 9/1998 | Milstein et al. | |
| 5,820,881 A | 10/1998 | Milstein | |
| 5,824,345 A | 10/1998 | Milstein | |
| 5,840,340 A | 11/1998 | Milstein et al. | |
| 5,863,944 A | 1/1999 | Leone-Bay et al. | |
| 5,866,536 A | 2/1999 | Leone-Bay et al. | |
| 5,876,710 A | 3/1999 | Leone-Bay et al. | |
| 5,879,681 A | 3/1999 | Leone-Bay et al. | |
| 5,883,088 A | 3/1999 | Bernstein | |
| 5,935,601 A | 8/1999 | Leone-Bay et al. | |
| 5,939,381 A | 8/1999 | Leone-Bay et al. | |
| 5,955,503 A | 9/1999 | Leone-Bay et al. | |
| 5,958,451 A | 9/1999 | Chen et al. | |
| 5,962,710 A | 10/1999 | Gschneidner et al. | |
| 5,965,121 A | 10/1999 | Leone-Bay et al. | |
| 5,968,922 A | 10/1999 | Bernstein | |
| 5,972,387 A | 10/1999 | Milstein et al. | |
| 5,976,569 A | 11/1999 | Milstein | |
| 5,981,518 A | 11/1999 | Bernstein | |
| 5,989,539 A | 11/1999 | Leone-Bay et al. | |
| 5,990,166 A | 11/1999 | Leone-Bay et al. | |
| 5,998,397 A | 12/1999 | Bernstein | |
| 6,001,347 A | 12/1999 | Leone-Bay et al. | |
| 6,004,951 A | 12/1999 | Bernstein | |
| 6,048,851 A | 4/2000 | Bernstein | |
| 6,051,258 A | 4/2000 | Kantor | |
| 6,051,561 A | 4/2000 | Leone-Bay et al. | |
| 6,054,145 A * | 4/2000 | Vromans et al. | 424/489 |
| 6,060,513 A | 5/2000 | Leone-Bay et al. | |
| 6,071,510 A | 6/2000 | Leone-Bay et al. | |
| 6,084,112 A | 7/2000 | Ho et al. | |
| 6,087,354 A | 7/2000 | Bernstein | |
| 6,090,958 A | 7/2000 | Leone-Bay et al. | |
| 6,099,856 A | 8/2000 | Milstein et al. | |
| 6,100,285 A | 8/2000 | Kantor | |
| 6,100,298 A | 8/2000 | Leone-Bay et al. | |
| 6,165,514 A | 12/2000 | Bockman et al. | |
| 6,180,140 B1 | 1/2001 | Leone-Bay et al. | |
| 6,221,367 B1 | 4/2001 | Milstein et al. | |
| 6,242,495 B1 | 6/2001 | Leone-Bay et al. | |

(Continued)

FOREIGN PATENT DOCUMENTS

WO    WO-9612474    5/1996
WO    WO-9612475    5/1996

(Continued)

OTHER PUBLICATIONS

Ibrahim et al. (Journal of Pharmaceutical Sciences vol. 74, No. 5, May 1985 pp. 575-577).*

(Continued)

*Primary Examiner* — Patricia Duffy
*Assistant Examiner* — Garen Gotfredson
(74) *Attorney, Agent, or Firm* — Blank Rome LLP

(57) ABSTRACT

The present invention relates to stable pharmaceutical formulations that include a delivery agent and/or pharmaceutically acceptable salt thereof.

16 Claims, 1 Drawing Sheet

(56) References Cited

U.S. PATENT DOCUMENTS

| | | |
|---|---|---|
| 6,245,359 B1 | 6/2001 | Milstein et al. |
| 6,313,088 B1 | 11/2001 | Leone-Bay et al. |
| 6,331,318 B1 | 12/2001 | Milstein |
| 6,344,213 B1 | 2/2002 | Leone-Bay et al. |
| 6,346,242 B1 | 2/2002 | Leone-Bay et al. |
| 6,358,504 B1 | 3/2002 | Leone-Bay et al. |
| 6,375,983 B1 | 4/2002 | Kantor et al. |
| 6,384,278 B1 | 5/2002 | Tang et al. |
| 6,391,303 B1 | 5/2002 | Haas et al. |
| 6,395,774 B1 | 5/2002 | Milstein |
| 6,399,798 B2 | 6/2002 | Gschneidner et al. |
| 6,413,550 B1 | 7/2002 | Milstein et al. |
| 6,428,780 B2 | 8/2002 | Leone-Bay et al. |
| 6,440,929 B1 | 8/2002 | Milstein et al. |
| 6,461,545 B1 | 10/2002 | Kantor |
| 6,461,643 B2 | 10/2002 | Milstein et al. |
| 6,525,020 B2 | 2/2003 | Leone-Bay et al. |
| 6,558,706 B2 | 5/2003 | Kantor et al. |
| 6,562,870 B1 | 5/2003 | Von Hoff et al. |
| 6,610,329 B2 | 8/2003 | Santiago et al. |
| 6,623,731 B2 | 9/2003 | Leone-Bay et al. |
| 6,627,228 B1 | 9/2003 | Milstein et al. |
| 6,642,411 B1 | 11/2003 | Leone-Bay et al. |
| 6,646,162 B2 | 11/2003 | Tang et al. |
| 6,663,887 B2 | 12/2003 | Leone-Bay et al. |
| 6,663,898 B2 | 12/2003 | Milstein |
| 6,693,208 B2 | 2/2004 | Gschneidner et al. |
| 6,693,898 B1 | 2/2004 | Su et al. |
| 6,699,467 B2 | 3/2004 | Leone-Bay et al. |
| 2001/0003001 A1 | 6/2001 | Leone-Bay et al. |
| 2001/0039258 A1 | 11/2001 | Milstein et al. |
| 2002/0001591 A1 | 1/2002 | Santiago et al. |
| 2002/0013497 A1 | 1/2002 | Gschneidner et al. |
| 2002/0028250 A1 | 3/2002 | Milstein |
| 2002/0040061 A1 | 4/2002 | Tang et al. |
| 2002/0052422 A1 | 5/2002 | Milstein et al. |
| 2002/0065255 A1 | 5/2002 | Bay et al. |
| 2002/0102286 A1 | 8/2002 | Kantor et al. |
| 2002/0119910 A1 | 8/2002 | Leone-Bay et al. |
| 2002/0120009 A1 | 8/2002 | Leone-Bay et al. |
| 2002/0127202 A1 | 9/2002 | Leone-Bay et al. |
| 2002/0155993 A1 | 10/2002 | Milstein |
| 2003/0008900 A1 | 1/2003 | Leone-Bay et al. |
| 2003/0012817 A1 | 1/2003 | Milstein et al. |
| 2003/0031727 A1* | 2/2003 | Hahn et al. .............. 424/617 |
| 2003/0045579 A1 | 3/2003 | Leone-Bay et al. |
| 2003/0072740 A1 | 4/2003 | Milstein et al. |
| 2003/0078302 A1 | 4/2003 | Leone-Bay et al. |
| 2003/0133953 A1 | 7/2003 | Milstein et al. |
| 2003/0157019 A1* | 8/2003 | Kushida et al. .......... 423/648.1 |
| 2003/0198658 A1 | 10/2003 | Milstein |
| 2003/0225300 A1 | 12/2003 | Leone-Bay et al. |
| 2003/0232085 A1 | 12/2003 | Milstein et al. |
| 2003/0235612 A1 | 12/2003 | Leone-Bay et al. |
| 2004/0022856 A1 | 2/2004 | Sarubbi et al. |
| 2004/0062773 A1 | 4/2004 | Santiago et al. |
| 2004/0068013 A1 | 4/2004 | Leone-Bay et al. |
| 2004/0106825 A1 | 6/2004 | Bay et al. |
| 2004/0110839 A1 | 6/2004 | Leone-Bay et al. |
| 2005/0277621 A1 | 12/2005 | Gschneidner |

FOREIGN PATENT DOCUMENTS

| | | |
|---|---|---|
| WO | WO-9621464 | 7/1996 |
| WO | WO-9630036 | 10/1996 |
| WO | WO-9633699 | 10/1996 |
| WO | WO-9639835 | 12/1996 |
| WO | WO-9640070 | 12/1996 |
| WO | WO-9640076 | 12/1996 |
| WO | WO-9710197 | 3/1997 |
| WO | WO-9731938 | 9/1997 |
| WO | WO-9736480 | 10/1997 |
| WO | WO-9747288 | 12/1997 |
| WO | WO-9821951 | 5/1998 |
| WO | WO-9825589 | 6/1998 |
| WO | WO-9834632 | 8/1998 |
| WO | WO-9849135 | 11/1998 |
| WO | WO-9850341 | 11/1998 |
| WO | WO-9916427 | 4/1999 |
| WO | WO-0006184 | 2/2000 |
| WO | WO-0006534 | 2/2000 |
| WO | WO-0007979 | 2/2000 |
| WO | WO-0040203 | 7/2000 |
| WO | WO-00/46182 A1 | 8/2000 |
| WO | WO-0046182 | 8/2000 |
| WO | WO-0046812 | 8/2000 |
| WO | WO-0047188 | 8/2000 |
| WO | WO-0048589 | 8/2000 |
| WO | WO-0050386 | 8/2000 |
| WO | WO-00/59863 | 10/2000 |
| WO | WO-0059480 | 10/2000 |
| WO | WO-0059863 | 10/2000 |
| WO | WO-0132130 | 5/2001 |
| WO | WO-0132596 | 5/2001 |
| WO | WO-0134114 | 5/2001 |
| WO | WO-0144199 | 6/2001 |
| WO | WO-0151454 | 7/2001 |
| WO | WO-0170219 | 9/2001 |
| WO | WO-0192206 | 12/2001 |
| WO | WO-0202509 | 1/2002 |
| WO | WO-0215959 | 2/2002 |
| WO | WO-0216309 | 2/2002 |
| WO | WO-0219969 | 3/2002 |
| WO | WO-0220466 | 3/2002 |
| WO | WO-02069937 | 9/2002 |
| WO | WO-02070438 | 9/2002 |
| WO | WO-02100338 | 12/2002 |
| WO | WO-03026582 | 4/2003 |
| WO | WO-03045306 | 6/2003 |
| WO | WO-03045331 | 6/2003 |
| WO | WO-03/057170 | 7/2003 |
| WO | WO-03/057650 A1 | 7/2003 |
| WO | WO-2004/062587 | 7/2004 |
| WO | WO-2004/080401 | 9/2004 |
| WO | WO-2006/072070 | 7/2006 |

OTHER PUBLICATIONS

Provisional U.S. Appl. No. 60/619,418, filed Oct. 15, 2004.
Provisional U.S. Appl. No. 60/569,476, filed May 6, 2004.
Gennaro, Ed., Remington's Pharmaceutical Sciences (17th Ed. 1985), pp. 1317, 1318, 1420, 1421, 1478, 1479, 1481, 1585, 1596-1614, 1625, 1626.

\* cited by examiner

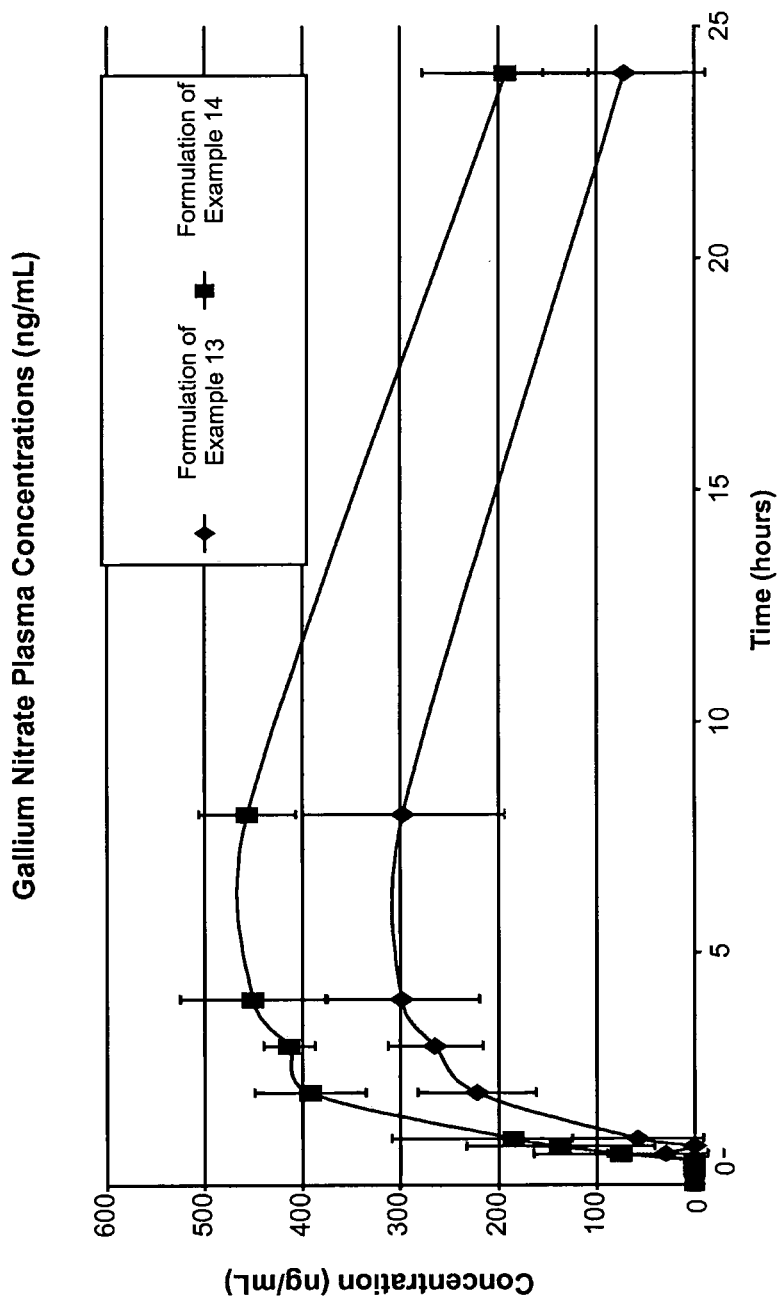

GALLIUM NITRATE FORMULATIONS

CROSS REFERENCE TO PRIOR APPLICATIONS

This application is the U.S. national phase of International Application No. PCT/US07/072373, filed Jun. 28, 2007, which claims the benefit of U.S. Provisional Application No. 60/817,561, filed Jun. 28, 2006, and U.S. Provisional Application No. 60/881,044, filed Jan. 17, 2007, both of which are hereby incorporated by reference. The International Application was published in English on Jan. 3, 2008 as WO 2008/003050 under PCT Article 21(2)

FIELD OF THE INVENTION

The present invention relates to stable pharmaceutical formulations containing a pharmaceutically acceptable gallium salt (such as gallium nitrate), and a delivery agent.

BACKGROUND OF THE INVENTION

Conventional means for delivering drugs are often severely limited by biological, chemical, and physical barriers. Typically, these barriers are imposed by the environment through which delivery occurs, the environment of the target for delivery, and/or the target itself. Examples of physical barriers include the skin, lipid bi-layers and various organ membranes that are relatively impermeable to certain drugs but must be traversed before reaching a target, such as the circulatory system. Chemical barriers include, but are not limited to, pH variations in the gastrointestinal (GI) tract and degrading enzymes.

These barriers are of particular significance in the design of oral delivery systems. Oral delivery of many drugs would be the route of choice for administration if not for biological, chemical, and physical barriers that prevent, restrict or reduce the passage of drugs. Among the numerous agents in this category are gallium salts.

U.S. Pat. No. 4,529,593 discloses a method of preventing or treating a disorder associate with accelerated loss of calcium from bone in a human individual by administering to the individual a pharmaceutically acceptable gallium compound, such as gallium nitrate.

U.S. Pat. No. 4,704,277 discloses a method of increasing bone growth, decreasing hydroxyapatite solubility, increasing the size and/or the perfection of hydroxyapatite crystals in bone, and/or increasing the tensile strength of bone by administering to an individual a pharmaceutically acceptable gallium compound, such as gallium nitrate.

Gallium nitrate is currently marketed as Ganite™, an intravenous injection, for the treatment of clearly symptomatic cancer-related hypercalcemia that has not responded to adequate hydration. Gallium nitrate is not currently available as an oral formulation due to its poor oral bioavailability. According to the FDA approved labeling for Ganite™, gallium nitrate exerts a hypocalcemic effect by inhibiting calcium resorption from bone, possibly by reducing increased bone turnover.

Additionally, according to the FDA approved labeling for Ganite™ hypercalcemia is a common problem in hospitalized patients with malignancy. It may affect 10-20% of patients with cancer. Different types of malignancy seem to vary in their propensity to cause hypercalcemia. A higher incidence of hypercalcemia has been observed in patients with non-small cell lung cancer, breast cancer, multiple myeloma, kidney cancer, and cancer of head and neck. Hypercalcemia of malignancy seems to result from an imbalance between the net resorption of bone and urinary excretion of calcium. Patients with extensive osteolytic bone metastases frequently develop hypercalcemia. This type of hypercalcemia is common with primary breast cancer. Some of these patients have been reported to have increased renal tubular calcium resorption. Breast cancer cells have been reported to produce several potential bone-resorbing factors which stimulate the local osteoclast activity. Humoral hypercalcemia is common with the solid tumors of the lung, head and neck, kidney, and ovaries. Systemic factors (e.g., PTH-rP) produced either by the tumor or host cells have been implicated for the altered calcium fluxes between the extracellular fluid, the kidney, and the skeleton. About 30% of patients with myeloma develop hypercalcemia associated with extensive osteolytic lesions and impaired glomerular filtration. Myeloma cells have been reported to produce local factors that stimulate adjacent osteoclasts. Hypercalcemia may produce a spectrum of signs and symptoms including: anorexia, lethargy, fatigue, nausea, vomiting, constipation, polyuria, dehydration, renal insufficiency, impaired mental status, coma, EKG abnormalities and cardiac arrest.

One type of hypercalcemia, "Non-PTH-Mediated Hypercalcemia", is theorized to result from an increase in osteoclastic activity. While malignant disorders are a common cause of this type of hypercalcemia, it may also be due to other causes. Granulomatous disorders with high levels of calcitriol may be found in patients with sarcoidosis, berylliosis, tuberculosis, leprosy, coccidioidomycosis, and histoplasmosis. Iatrogenic disorders of calcium levels may increase secondary to the ingestion of many medications (e.g. thiazide diuretics, calcium carbonate, hypervitaminosis D, hypervitaminosis A, lithium, milk-alkali syndrome and thephylline toxicity). Chronic renal failure, post transplant states and hemodialysis may also cause hypercalcemia.

Hypercalcemia may also result from Primary Hyperparathyroidiam. Plasma calcium is maintained within the reference range by a complex interplay of 3 major hormones, parathyroid hormone (PTH), 1,25-dihydroxyvitamin D (ie, calcitriol), and calcitonin. These 3 hormones act primarily at bone, kidney, and small intestine sites to maintain appropriate calcium levels. In most primary hyperparathyroidism cases, the calcium elevation is caused by increased intestinal calcium absorption. This is mediated by the PTH-induced calcitriol synthesis that enhances calcium absorption. The increase in serum calcium results in an increase in calcium filtration at the kidney. Because of PTH-mediated absorption of calcium at the distal tubule, less calcium is excreted than might be expected. Generally, in PTH-mediated hypercalcemia, bones do not play an active role because most of the PTH-mediated osteoclast activity that breaks down bone is offset by hypercalcemic-induced bone deposition.

International Publication No. WO 2006/072070 describes pharmaceutical formulations containing a pharmaceutically acceptable gallium salt (such as gallium nitrate), a delivery agent, and optionally, one or more chemotherapeutic agents and/or adjunctive chemotherapeutic agents.

A goal of treatment is to stabilize and reduce the calcium level, increase urinary calcium excretion, inhibit osteoclast activity in the bone, and treat underlying causes when possible.

There is a need for improved oral delivery systems for gallium salts which provide sufficient bioavailability to treat hypercalcemia.

SUMMARY OF THE INVENTION

A major problem encountered with the development of oral formulations of gallium salts is an oxidation reaction that occurs in the presence of gallium nitrate and the delivery agent compound. The presence of water and trace amounts of nitric acid both associated with the gallium nitrate are believed to contribute to the oxidation reaction. Oxidation reactions, evidenced by brown discoloration of the dosage form, results in a delivery agent and/or gallium salt degradation product, which is not desired. For example, the conversion of gallium nitrate to poorly soluble gallium oxide or gallium hydroxide degradation products impairs the absorption of the gallium molecule.

The present invention provides a method of preparing a stable pharmaceutical formulation comprising at least one delivery agent and a pharmaceutically acceptable gallium salt that includes at least one of the following steps: (i) mixing the delivery agent and pharmaceutically acceptable gallium salt via a low-shear mixing technique, (ii) preparing wet granules comprising a gallium salt and optionally separate wet granules comprising a delivery agent and drying, preferably gently, the wet granules, (iii) preparing tablets comprising a gallium salt and a delivery agent using a low compression pressure, and (iv) introducing an excipient to the pharmaceutical formulation in an amount effective to prevent discoloration of the pharmaceutical formulation. In each of these embodiments, the delivery agent and gallium salt are preferably incorporated into the pharmaceutical formulation in such a manner that contact between them is minimized if not completely eliminated during preparation and in the final product.

The present invention also provides a method of preparing a pharmaceutical formulation that includes at least one delivery agent and a pharmaceutically acceptable gallium salt that includes the steps of preparing granules consisting essentially of (a) a pharmaceutically acceptable gallium salt and optionally (b) intragranular excipients, optionally preparing a granule consisting essentially of (a) a delivery agent compound and optionally (b) intragranular excipients, mixing the gallium salt granules and a delivery agent, where the delivery agent is in the form of granules or some other form, and forming a pharmaceutical formulation with the mixture, e.g., by tableting the mixture of granules or filling a capsule with the mixture of granules.

The present invention also provides a method of preparing a pharmaceutical formulation that includes at least one delivery agent and a pharmaceutically acceptable gallium salt that includes the steps of dissolving a gallium salt in water to form a gallium salt solution, forming a separate admixture that contains at least one intragranular excipient and/or delivery agent compound and granulating the admixture using the gallium salt solution as a granulation solution. Preferably, a base, such as sodium citrate, is added to the aqueous gallium salt solution and/or the admixture, for example, to neutralize any excess nitric acid present from gallium nitrate.

The present invention also provides a pharmaceutical composition comprising a gallium salt and a delivery agent compound, and an excipient selected from a diluent, a highly porous agent, an absorbent agent, a hydrophilic polymer, a compressibility aid, a binding agent, a disintegrant, a dessicant, an antioxidant agent, or any combination thereof.

BRIEF DESCRIPTION OF THE DRAWING

FIG. 1 shows Examples 13 and 14 plasma concentrations of Gallium Nitrate (ng/mL) over time (hrs) in dogs.

DETAILED DESCRIPTION OF THE INVENTION

Definitions

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviations, per practice in the art. Alternatively, "about" with respect to the formulations can mean a range of up to 10%, preferably up to 5%.

The terms "alkyl", "alkenyl", "alkoxy", "alkylene", "alkenylene", "alkyl(arylene)", and "aryl(alkylene)" include, but are not limited to, linear and branched alkyl, alkenyl, alkoxy, alkylene, alkenylene, alkyl(arylene), and aryl(alkylene) groups, respectively.

The phrase "pharmaceutically acceptable" refers to compounds or compositions that are physiologically tolerable and do not typically produce an allergic or similar untoward reaction, such as gastric upset, dizziness and the like, when administered to a mammal.

An "effective amount of gallium salt" or "effective amount of gallium nitrate" means the amount of gallium salt or salts, or gallium nitrate (including its solvates, active metabolites, prodrugs, or racemates or enantiomers thereof (assuming the salt has a chiral center)) that, when administered to a mammal for treating or preventing a state, disorder or condition is sufficient to effect such treatment or prevention. The "effective amount" will vary depending on the active ingredient, the state, disorder, or condition to be treated and its severity, and the age, weight, physical condition and responsiveness of the mammal to be treated. According to one embodiment of the present invention, a therapeutically effective amount of a gallium salt is an amount effective to treat any one of the above mentioned disorders. The gallium salt may be augmented with a second medication (such as a loop diuretic, a chemotherapeutic agent, or adjunctive chemotherapeutic agent to treat any of the aforementioned disorders, such as malignancies and hypercalcemia.

An "effective amount of delivery agent" refers to an amount of the delivery agent that promotes the absorption of a desired amount of the gallium salt from, for example, the gastrointestinal tract.

An "effective amount of the pharmaceutical formulation" is an amount of the pharmaceutical formulation described which is effective to treat or prevent a condition in a subject to whom it is administered over some period of time, e.g., provides a therapeutic effect during a desired dosing interval. Generally, an effective amount of the pharmaceutical formulation includes amounts of gallium salt and at least one delivery agent to treat or prevent the desired condition over a desired period of time (i.e., an effective amount of delivery agent and an effective amount of gallium salt).

As used herein, the term "treat" includes one or more of the following:

(a) arresting, delaying the onset (i.e., the period prior to clinical manifestation of a disorder) and/or reducing the risk of developing or worsening a disorder;

(b) relieving or alleviating at least one symptom of a disorder in a mammal, including for example, hypercalcemia; or (c) relieving or alleviating the intensity and/or duration of a manifestation of a disorder experienced by a mammal including, but not limited to, those which are in response to a given stimulus (e.g., pressure, tissue injury or cold temperature). The term "treat" also includes prophylactically preventing, curing, healing, alleviating, relieving, altering, remedying, ameliorating, improving, or affecting a condition (e.g., a disease), the symptoms of the condition, or the predisposition toward the condition.

The term "sustained release" as used herein refers to the release of an active ingredient over an extended period of time leading to lower peak plasma concentrations and a prolonged $T_{max}$ as compared to "immediate release" formulations of the same active ingredient.

The term "bioavailability" refers to the rate and extent to which the active ingredient (gallium salt) or active moiety is absorbed from a drug product and becomes systematically available.

The term "polymorph" refers to crystallographically distinct forms of a substance.

The term "hydrate" as used herein includes, but is not limited to, (i) a substance containing water combined in the molecular form and (ii) a crystalline substance containing one or more molecules of water of crystallization or a crystalline material containing free water.

The term "SNAC" as used herein refers to N-(8-[2-hydroxybenzoyl]-amino) caprylic acid and pharmaceutically acceptable salts thereof, including its monosodium and disodium salt. The term "SNAC free acid" refers to N-(8-[2-hydroxybenzoyl]-amino) caprylic acid. Unless otherwise noted, the term "SNAC" refers to all forms of SNAC, including all amorphous and polymorphic forms of SNAC, such as SNAC trihydrate and those described in U.S. Ser. Nos. 60/619,418 and 60/569,476, both of which are hereby incorporated by reference. The term "SNAC trihydrate" as used herein refers to a crystalline form of SNAC in which three molecules of water are associated with each molecule of SNAC. SNAC can be prepared by the procedures described in U.S. Pat. No. 5,650,386 and International Publication Nos. WO00/46182 and WO00/59863.

The term "SNAD" as used herein refers to N-(8-[2-hydroxybenzoyl]-amino) decanoic acid and pharmaceutically acceptable salts thereof, including its monosodium salt. Unless otherwise noted, the term "SNAD" refers to all forms of SNAD, including all amorphous and polymorphic forms of SNAD.

The term "4-CNAB" as used herein refers to 4-[(4-chloro-2-hydroxy-benzoyl)amino]butanoic acid (also known as 4-[(2-hydroxy-4-chlorobenzoyl)amino]butanoate) and pharmaceutically acceptable salts thereof, including its sodium salt (e.g., monosodium salt). Unless otherwise noted, the term "4-CNAB" refers to all forms of 4-CNAB, including all amorphous and polymorphic forms of 4-CNAB. The term "sodium 4-CNAB" and "mono-sodium 4-CNAB" refer to monosodium 4-[(2-hydroxy-4-chlorobenzoyl)amino]butanoate, including anhydrous, monohydrate, and isopropanol solvates thereof and amorphous and polymorphic forms thereof (including those described in International Publication No. WO 03/057650 which is hereby incorporated by reference), unless otherwise indicated.

The term "solvate" as used herein includes, but is not limited to, a molecular or ionic complex of molecules or ions of a solvent with molecules or ions of a delivery agent or gallium salt.

The term "delivery agent" refers to any of the delivery agent compounds disclosed or incorporated by reference herein.

The term "adjunctive chemotherapeutic agent" includes agents which treat, alleviate, relieve, or ameliorate the side effects of chemotherapeutic agents. Such agents include those which modify blood cell growth and maturation. Examples of adjunctive chemotherapeutic agents include, but are not limited to, filgrastim and erythropoietin.

The term "gallium salt" includes gallium salt or salts, gallium complexes and active metabolites, prodrugs, racemates, enantiomers, and hydrates thereof.

The term "chemotherapeutic agent" includes any agent which treats, prevents, cures, heals, alleviates, relieves, alters, remedies, ameliorates, improves, or affects malignancies and their metastasis. Examples of such agents (also known as "antineoplastic agents") include, but are not limited to, prednisone, fluorouracil (e.g., 5-fluorouracil (5-FU)), anastrozole, bicalutamide, carboplatin, cisplatin, chlorambucil, docetaxel, doxorubicin, flutamide, interferon-alpha, letrozole, leuprolide, megestrol, mitomycin, paclitaxel, plicamycin (Mithracin™), tamoxifen, thiotepa, topotecan, valrubicin, vinvlastin, vincristine, and any combination of any of the foregoing.

Delivery Agent Compounds

Suitable delivery agents include those having the following structure and pharmaceutically acceptable salts thereof:

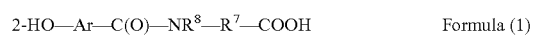

$$2\text{-HO—Ar—C(O)—NR}^8\text{—R}^7\text{—COOH} \qquad \text{Formula (1)}$$

wherein
Ar is phenyl or naphthyl, optionally substituted with OH, halogen, $C_1$-$C_4$ alkyl, $C_1$-$C_4$ alkenyl, $C_1$-$C_4$ alkoxy or $C_1$-$C_4$ haloalkoxy;

$R^7$ is $C_4$-$C_{20}$ alkyl, $C_4$-$C_{20}$ alkenyl, phenyl, naphthyl, ($C_1$-$C_{10}$ alkyl) phenyl, ($C_1$-$C_{10}$ alkenyl)phenyl, ($C_1$-$C_{10}$ alkyl) naphthyl, ($C_1$-$C_{10}$ alkenyl) naphthyl, phenyl($C_1$-$C_{10}$ alkyl), phenyl($C_1$-$C_{10}$alkenyl), naphthyl($C_1$-$C_{10}$alkyl), or naphthyl($C_1$-$C_{10}$alkenyl);

$R^8$ is hydrogen, $C_1$ to $C_4$ alkyl, $C_2$ to $C_4$ alkenyl, $C_1$ to $C_4$ alkoxy, $C_1$-$C_4$ or haloalkoxy;

$R^7$ is optionally substituted with $C_1$ to $C_4$ alkyl, $C_2$ to $C_4$ alkenyl, $C_1$ to $C_4$ alkoxy, $C_1$-$C_4$ haloalkoxy, —OH, —SH, and —CO$_2$R$^9$ or any combination thereof;

$R^9$ is hydrogen, $C_1$ to $C_4$ alkyl or $C_2$ to $C_4$ alkenyl; and $R^7$ is optionally interrupted by oxygen, nitrogen, sulfur or any combination thereof; with the proviso that the compounds are not substituted with an amino group in the position alpha to the acid group or salts thereof.

According to one embodiment, Ar is substituted with a halogen.

Preferably, $R^7$ is $C_4$-$C_{20}$ alkyl or phenyl($C_1$-$C_{10}$alkyl). More preferably $R^7$ is $C_5$-$C_{10}$alkyl or phenyl($C_2$alkyl). Most preferably, $R^7$ is $C_7$-$C_9$alkyl or phenyl($C_2$alkyl).

Other suitable delivery agents include those having the following structure and pharmaceutically acceptable salts thereof:

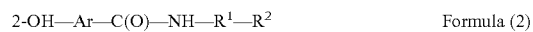

$$2\text{-OH—Ar—C(O)—NH—R}^1\text{—R}^2 \qquad \text{Formula (2)}$$

wherein
Ar is phenyl or naphthyl;
Ar is optionally substituted with $C_1$-$C_4$ alkyl, $C_1$-$C_4$ alkoxy, $C_2$-$C_4$ alkenyl, $C_2$-$C_4$ alkynyl, aryl, aryloxy, a heterocyclic ring, $C_5$-$C_7$ carbocylic ring, halogen, —OH, —SH, CO$_2$R$^6$, —NR$^7$R$^8$, or —N$^+$R$^7$R$^8$R$^9$Y$^-$;

(a) $R^1$ is $C_1$-$C_{16}$ alkylene, $C_2$-$C_{16}$ alkenylene, $C_2$-$C_{16}$ alkynylene, $C_6$-$C_{16}$ arylene, ($C_1$-$C_{16}$alkyl)arylene, or aryl ($C_1$-$C_{16}$alkylene);

$R^2$ is —NR$^3$R$^4$ or —N$^+$R$^3$R$^4$R$^5$Y$^-$;

$R^3$ and $R^4$ are independently hydrogen; oxygen; hydroxy; substituted or unsubstituted $C_1$-$C_{16}$ alkyl; substituted or unsubstituted $C_2$-$C_{16}$ alkenyl; substituted or unsubstituted $C_2$-$C_{16}$ alkynyl; substituted or unsubstituted aryl; substituted or unsubstituted alkylcarbonyl; substituted or unsubstituted arylcarbonyl; substituted or unsubstituted alkanesulfinyl; substituted or unsubstituted arylsulfinyl; substituted or unsubstituted alkanesulfonyl; substituted or unsubstituted arylsulfonyl; substituted or unsubstituted alkoxycarbonyl; substituted or unsubstituted aryloxycarbonyl;

$R^5$ is independently hydrogen; substituted or unsubstituted $C_1$-$C_{16}$ alkyl; substituted or unsubstituted $C_2$-$C_{16}$ alkenyl; substituted or unsubstituted $C_2$-$C_{16}$ alkynyl; substituted or unsubstituted aryl; substituted or unsubstituted alkylcarbonyl; substituted or unsubstituted arylcarbonyl; substituted or unsubstituted alkanesulfinyl; substituted or unsubstituted arylsulfinyl; substituted or unsubstituted alkanesulfonyl; substituted or unsubstituted arylsulfonyl; substituted or unsubstituted alkoxycarbonyl; substituted or unsubstituted aryloxycarbonyl;

(b) $R^1$, $R^2$, and $R^5$ are as defined above; and $R^3$ and $R^4$ are combined to form a 5, 6 or 7-membered heterocyclic ring; or 5, 6 or 7-membered heterocyclic ring substituted with a $C_1$-$C_6$ alkyl, $C_1$-$C_6$ alkoxy, aryl, aryloxy, oxo group or carbocyclic ring; or (c) $R^2$ and $R^5$ are as defined above; and $R^1$ and $R^3$ are combined to form a 5, 6 or 7-membered heterocyclic ring; or 5, 6 or 7-membered heterocyclic ring substituted with a $C_1$-$C_6$ alkyl, alkoxy, aryl, aryloxy, or oxo group or carbocyclic ring;

$R^4$ is hydrogen; oxygen; hydroxy; substituted or unsubstituted $C_1$-$C_{16}$ alkyl; substituted or unsubstituted $C_2$-$C_{16}$ alkenyl; substituted or unsubstituted $C_2$-$C_{16}$ alkynyl; substituted or unsubstituted aryl; substituted or unsubstituted alkylcarbonyl; substituted or unsubstituted arylcarbonyl; substituted or unsubstituted alkanesulfinyl; substituted or unsubstituted arylsulfinyl; substituted or unsubstituted alkanesulfonyl; substituted or unsubstituted arylsulfonyl; substituted or unsubstituted alkoxycarbonyl; substituted or unsubstituted aryloxycarbonyl;

$R^6$ is hydrogen; $C_1$-$C_4$alkyl; $C_1$-$C_4$alkyl substituted halogen or —OH; $C_2$-$C_4$alkenyl; or $C_2$-$C_4$alkenyl substituted halogen or —OH;

$R^7$, $R^8$, and $R^9$ are independently hydrogen; oxygen; $C_1$-$C_4$ alkyl; $C_1$-$C_4$ alkyl substituted with halogen or —OH; $C_2$-$C_4$alkenyl; or $C_2$-$C_4$alkenyl substituted with halogen or —OH; and Y is halogen, hydroxide, sulfate, nitrate, phosphate, alkoxy, perchlorate, tetrafluoroborate, or carboxylate. A non-limiting example of a suitable carboxylate is acetate.

The term "substituted" as used herein with respect to the compounds of formula (2) includes, but is not limited to, hydroxyl and halogen.

In one embodiment, Ar is unsubstituted phenyl or phenyl substituted with one or more of $C_1$-$C_4$ alkyl, $C_1$-$C_4$ alkoxy, or halogen. More preferably, Ar is a phenyl substituted with methoxy, Cl, F or Br, and even more preferably, Ar is a phenyl substituted with Cl.

In another embodiment, $R^1$ is $C_1$-$C_{12}$ alkyl, $C_2$-$C_8$ alkyl, $C_2$-$C_6$ alkyl, or $C_6$ alkyl.

In another embodiment, $R^3$ and $R^4$ are independently H or $C_1$-$C_2$ alkyl; or further $R^3$ and $R^4$ are not both H; or further $R^3$ and $R^4$ are independently methyl or ethyl; and more preferably $R^3$ and $R^4$ are both methyl.

Other suitable delivery agents include those having the following structure and pharmaceutically acceptable salts thereof:

Formula (3)

wherein
$R^1$, $R^2$, $R^3$, and $R^4$ are independently hydrogen, —OH, —NR$^6$R$^7$, halogen, $C_1$-$C_4$ alkyl, or $C_1$-$C_4$ alkoxy;

$R^5$ is a substituted or unsubstituted $C_2$-$C_{16}$ alkylene, substituted or unsubstituted $C_2$-$C_{16}$ alkenylene, substituted or unsubstituted $C_1$-$C_{12}$ alkyl(arylene), or substituted or unsubstituted aryl($C_1$-$C_{12}$ alkylene); and $R^6$ and $R^7$ are independently hydrogen, oxygen, or $C_1$-$C_4$ alkyl.

The term "substituted" as used with respect to formula (3) includes, but is not limited to, substitution with any one or any combination of the following substituents: halogens, hydroxide, $C_1$-$C_4$ alkyl, and $C_1$-$C_4$ alkoxy.

Other suitable delivery agents include those having the following structure and pharmaceutically acceptable salts thereof:

Formula (4)

wherein
(a) $R^1$, $R^2$, $R^3$, and $R^4$ are independently H, —OH, halogen, $C_1$-$C_4$ alkyl, $C_1$-$C_4$ alkenyl, $C_1$-$C_4$alkoxy, —C(O)R$^8$, —NO$_2$, —NR$^9$R$^{10}$, or —N$^+$R$^9$R$^{10}$R$^{11}$(Y$^-$);

$R^8$ is hydrogen, —OH, $C_1$-$C_6$ alkyl, $C_1$-$C_4$ alkyl substituted with halogen or —OH, $C_2$-$C_4$ alkenyl unsubstituted or substituted with halogen or —OH, or —NR$^{14}$R$^{15}$;

$R^9$, $R^{10}$, $R^{11}$ are independently hydrogen, oxygen, $C_1$-$C_4$ alkyl unsubstituted or substituted with halogen or —OH, $C_2$-$C_4$ alkenyl unsubstituted or substituted with halogen or —OH;

Y is halide, hydroxide, sulfate, nitrate, phosphate, alkoxy, perchlorate, tetrafluoroborate, carboxylate, mesylate, fumerate, malonate, succinate, tartrate, acetate, gluconate, maleate;

$R^5$ is H, —OH, —NO$_2$, halogen, CF$_3$, —NR$^{14}$R$^{15}$, —N$^+$R$^{14}$R$^{15}$R$^{16}$(Y$^-$), amide, $C_1$-$C_{12}$ alkoxy, $C_1$-$C_{12}$ alkyl, $C_2$-$C_{12}$ alkenyl, carbamate, carbonate, urea, or —C(O)R$^{22}$; $R^5$ is optionally substituted with halogen, —OH, —SH, or —COOH; $R^5$ is optionally interrupted by O, N, S, or —C(O)—;

$R^{14}$, $R^{15}$, and $R^{16}$ are independently H or $C_1$-$C_{10}$ alkyl; $R^{22}$ is H, $C_1$-$C_6$ alkyl, —OH, —NR$^{14}$R$^{15}$;

$R^6$ is substituted or unsubstituted $C_1$-$C_{16}$ alkylene, $C_2$-$C_{16}$ alkenylene, $C_2$-$C_{16}$ alkynylene, $C_5$-$C_{16}$ arylene, ($C_1$-$C_{16}$ alkyl) arylene or aryl($C_1$-$C_{16}$ alkylene); $R^6$ is optionally substituted with $C_1$-$C_7$ alkyl or $C_1$-$C_7$ cycloalkyl;

$R^7$ is —$NR^{18}R^{19}$ or —$N^+R^{18}R^{19}R^{20}Y^-$;

$R^{18}$ and $R^{19}$ are independently hydrogen, oxygen, hydroxy, substituted or unsubstituted $C_1$-$C_{16}$ alkyl, substituted or unsubstituted $C_2$-$C_{16}$ alkenyl, substituted or unsubstituted $C_2$-$C_{16}$ alkynyl, substituted or unsubstituted aryl, substituted or unsubstituted alkylcarbonyl (e.g. substituted or unsubstituted ($C_{1-6}$ alkyl)carbonyl), substituted or unsubstituted arylcarbonyl, substituted or unsubstituted alkanesulfinyl (e.g. substituted or unsubstituted ($C_{1-6}$ alkane)sulfinyl), substituted or unsubstituted arylsulfinyl, substituted or unsubstituted alkanesulfonyl (e.g. substituted or unsubstituted ($C_{1-6}$ alkane)sulfonyl), substituted or unsubstituted arylsulfonyl, substituted or unsubstituted alkoxycarbonyl (e.g. substituted or unsubstituted ($C_{1-6}$ alkoxy)carbonyl), or substituted or unsubstituted aryloxyccarbonyl, or substituted or unsubstituted $C_5$-$C_7$ heterocyclic ring (i.e., 5, 6, or 7-membered heterocyclic ring), wherein the substitutions may be halogen or —OH; and $R^{20}$ is independently hydrogen, substituted or unsubstituted $C_1$-$C_{16}$ alkyl, substituted or unsubstituted $C_2$-$C_{16}$ alkenyl, substituted or unsubstituted $C_2$-$C_{16}$ alkynyl, substituted or unsubstituted aryl, substituted or unsubstituted alkylcarbonyl (e.g. substituted or unsubstituted ($C_{1-6}$ alkyl)carbonyl), substituted or unsubstituted arylcarbonyl, substituted or unsubstituted alkanesulfinyl (e.g. substituted or unsubstituted ($C_{1-6}$ alkane)sulfinyl), substituted or unsubstituted arylsulfinyl, substituted or unsubstituted alkanesulfonyl (e.g. substituted or unsubstituted ($C_{1-6}$ alkane) sulfonyl), substituted or unsubstituted arylsulfonyl, substituted or unsubstituted alkoxycarbonyl (e.g. substituted or unsubstituted ($C_{1-6}$ alkoxy)carbonyl), or substituted or unsubstituted aryloxycarbonyl; or (b) $R^1$-$R^{16}$ and $R^{20}$ are as defined above; and $R^{18}$ and $R^{19}$ combine to form a 5, 6, or 7-membered heterocyclic ring optionally interrupted with an oxo group and unsubstituted or substituted with $C_1$-$C_6$ alkyl, $C_1$-$C_6$ alkoxy, aryl, aryloxy, or carbocyclic ring.

According to one embodiment, $R^7$ is morpholino, morpholinium salt, or diethanolamino.

According to another embodiment, $R^6$ is a $C_1$-$C_{16}$ alkylene and $R^7$ is morpholino or a morpholinium salt. Preferably, $R^6$ is $C_4$-$C_{12}$ alkylene, such as an unsubstituted $C_4$-$C_{12}$ alkylene. More preferably, $R^6$ is $C_4$-$C_{10}$, $C_4$-$C_8$, or $C_6$-$C_8$ alkylene, such as an unsubstituted $C_4$-$C_{10}$, $C_4$-$C_8$, or $C_6$-$C_8$ alkylene. According to one embodiment, one of $R^1$-$R^5$ is hydroxy, for example, $R^1$ can be hydroxy.

According to yet another embodiment, when $R^6$ is a $C_1$-$C_{10}$ alkylene, at most one of $R^2$ and $R^4$ is halogen. According to another embodiment, $R^6$ is a $C_8$-$C_{16}$, $C_9$-$C_{16}$, $C_{10}$-$C_{16}$, or $C_{11}$-$C_{16}$ alkylene. For instance, $R^6$ may be a $C_8$, $C_9$, $C_{10}$, $C_{11}$, or $C_{12}$ alkylene (e.g., a normal $C_8$-$C_{12}$ alkylene). According to yet another embodiment, at most one of $R^1$ and $R^5$ is alkyl.

According to yet another embodiment, $R^1$ is hydroxy and $R^2$, $R^3$, $R^4$, and $R^5$ are independently hydrogen or halogen.

According to yet another embodiment, $R^2$ is hydroxy and $R^1$, $R^3$, $R^4$, and $R^5$ are independently hydrogen or halogen.

According to yet another embodiment, $R^3$ is hydroxy and $R^1$, $R^2$, $R^4$, and $R^5$ are independently hydrogen or halogen.

In a preferred embodiment, halogen is F, Cl or Br, more preferably F or Cl, and even more preferably Cl.

According to yet another embodiment, $R^6$ is $C_1$-$C_{16}$ alkylene, ($C_1$-$C_{16}$ alkyl) arylene or aryl($C_1$-$C_{16}$ alkylene). More preferably $R^6$ is $C_1$-$C_{12}$ alkylene, more preferably $C_3$-$C_{10}$ alkylene, more preferably $C_4$-$C_{10}$ or $C_4$-$C_8$ alkylene, and more preferably $C_6$-$C_8$ alkylene. More preferably, $R^6$ is unsubstituted.

According to yet another embodiment, $R^7$ is —$NR^{18}R^{19}$ and $R^{18}$ and $R^{19}$ are independently $C_1$-$C_4$ alkyl (e.g., methyl, ethyl, propyl, or butyl) substituted with —OH. In another embodiment, $R^7$ is —$NR^{18}R^{19}$ and $R^{18}$ and $R^{19}$ combine to form a six membered heterocyclic ring substituted with an oxo group.

According to one preferred embodiment, $R^1$ is hydrogen; $R^2$, $R^3$, and $R^4$ are independently hydrogen, halogen, —OH, or —$OCH_3$; $R^5$ is hydrogen, —OH, or —$C(O)CH_3$; $R^6$ is $C_1$-$C_{12}$ alkylene, and $R^7$ is $NR^{18}R^{19}$ wherein $R^{18}$ and $R^{19}$ combine to form a 5, 6, or 7 membered heterocyclic ring.

According to another preferred embodiment, one of $R^3$, $R^4$, and $R^5$ is hydroxy and the others are independently halogen or hydrogen; $R^1$ and $R^2$ are independently halogen or hydrogen; $R^6$ is $C_1$-$C_{16}$ alkylene; and $R^7$ is $NR^{18}R^{19}$ wherein $R^{18}$ and $R^{19}$ combine to form a 5, 6, or 7 membered heterocyclic ring. $R^6$ is preferably $C_6$-$C_{16}$, $C_6$-$C_{10}$, $C_8$-$C_{16}$, $C_{10}$-$C_{16}$, or $C_4$-$C_8$ alkylene, such as unsubstituted $C_6$-$C_{16}$, $C_6$-$C_{10}$, $C_8$-$C_{16}$, $C_{10}$-$C_{16}$, or $C_4$-$C_8$ alkylene. Preferably, $R^{18}$ and $R^{19}$ form a morpholino or imidazole.

In another preferred embodiment, $R^1$ is hydrogen; $R^2$, $R^3$, and $R^4$ are independently hydrogen, halogen, —OH, or —$OCH_3$; $R^5$ is hydrogen, —OH, or —$C(O)CH_3$; $R^6$ is $C_1$-$C_{12}$ alkylene; and $R^7$ is $N^+R^{18}R^{19}R^{20}$ ($Y^-$) wherein $R^{18}$ and $R^{19}$ are hydroxy substituted $C_1$-$C_{16}$ alkyl and $R^{20}$ is hydrogen.

In another preferred embodiment, $R^1$ is hydrogen; $R^2$, $R^3$, and $R^4$ are independently hydrogen, halogen, —OH, or —$OCH_3$; $R^5$ is hydrogen, —OH, or —$C(O)CH_3$; $R^6$ is $C_1$-$C_{12}$ alkylene; and $R^7$ is $N^+R^{18}R^{19}R^{20}$ ($Y^-$) wherein $R^{18}$ and $R^{19}$ are hydroxy substituted $C_1$-$C_{16}$ alkyl and $R^{20}$ is hydrogen.

In another preferred embodiment, $R^1$, $R^2$, $R^4$, $R^5$ are independently halogen or hydrogen; $R^3$ is —OH, or —$OCH_3$; and $R^7$ is $N^+R^{18}R^{19}R^{20}$ ($Y^-$) wherein $R^{18}$ and $R^{19}$ are hydroxy substituted $C_1$-$C_{16}$ alkyl and $R^{20}$ is hydrogen.

According to one preferred embodiment, $R^1$ is hydrogen; $R^2$, $R^3$, and $R^4$ are independently hydrogen, halogen, —OH, or —$OCH_3$; $R^5$ is hydrogen, —OH, or —$C(O)CH_3$; $R^6$ is $C_1$-$C_6$ alkylene or aryl substituted $C_1$-$C_{12}$ alkyl; and $R^7$ is —$NR^{18}R^{19}$ wherein $R^{18}$ and $R^{19}$ combine to form a 5, 6, or 7 membered heterocyclic ring or $N^+R^{18}R^{19}R^{20}$ ($Y^-$) wherein $R^{18}$ and $R^{19}$ are hydroxy substituted $C_1$-$C_{16}$ alkyl and $R^{20}$ is hydrogen.

In another preferred embodiment, the citrate salt of the delivery agent is used.

Other suitable delivery agents include those having the following structure and pharmaceutically acceptable salts thereof:

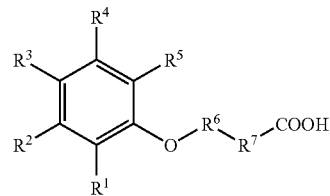

Formula (5)

wherein $R^1$, $R^2$, $R^3$, and $R^4$ are independently H, —OH, halogen, $C_1$-$C_4$ alkyl, $C_2$-$C_4$ alkenyl, $C_1$-$C_4$ alkoxy, —$C(O)R^8$, —$NO_2$, —$NR^9R^{10}$, or —$N^+R^9R^{10}R^{11}$ ($R^{12}$)$^-$;

$R^5$ is H, —OH, —NO$_2$, halogen, —CF$_3$, —NR$^{14}$R$^{15}$, —N$^+$R$^{14}$R$^{15}$R$^{16}$ (R$^{13}$)$^-$, amide, C$_1$-C$_{12}$ alkoxy, C$_1$-C$_{12}$ alkyl, C$_2$-C$_{12}$ alkenyl, carbamate, carbonate, urea, or —C(O)R$^{18}$;

$R^5$ is optionally substituted with halogen, —OH, —SH, or —COOH;

$R^5$ is optionally interrupted by O, N, S, or —C(O)—;

$R^6$ is a C$_1$-C$_{12}$ alkylene, C$_2$-C$_{12}$ alkenylene, or arylene;

$R^6$ is optionally substituted with a C$_1$-C$_4$ alkyl, C$_2$-C$_4$ alkenyl, C$_1$-C$_4$ alkoxy, —OH, —SH, halogen, —NH$_2$, or —CO$_2$R$^8$;

$R^6$ is optionally interrupted by O or N;

$R^7$ is a bond or arylene;

$R^7$ is optionally substituted with —OH, halogen, —C(O)CH$_3$, —NR$^{10}$R$^{11}$, or —N$^+$R$^{10}$R$^{11}$R$^{12}$ (R$^{13}$)$^-$;

$R^8$ is H, C$_1$-C$_4$ alkyl, C$_2$-C$_4$ alkenyl, or —NH$_2$;

$R^9$, $R^{10}$, $R^{11}$, and $R^{12}$ independently H or C$_1$-C$_{10}$ alkyl;

$R^{13}$ is a halide, hydroxide, sulfate, tetrafluoroborate, or phosphate; and $R^{14}$, $R^{15}$ and $R^{16}$ are independently H, C$_1$-C$_{10}$ alkyl, C$_1$-C$_{10}$ alkyl substituted with —COOH, C$_2$-C$_{12}$ alkenyl, C$_2$-C$_{12}$ alkenyl substituted with —COOH, —C(O)R$^{17}$;

$R^{17}$ is —OH, C$_1$-C$_{10}$ alkyl, or C$_2$-C$_{12}$ alkenyl; and $R^{18}$ is H, C$_1$-C$_6$ alkyl, —OH, —NR$^{14}$R$^{15}$, or N$^+$R$^{14}$R$^{15}$R$^{16}$ (R$^{13}$).

According one embodiment, (1) when $R^1$, $R^2$, $R^3$, $R^4$, and $R^5$ are H, and $R^7$ is a bond then $R^6$ is not a C$_1$-C$_6$, C$_9$ or C$_{10}$ alkyl;

(2) when $R^1$, $R^2$, $R^3$, and $R^4$ are H, $R^5$ is —OH, $R^7$ is a bond then $R^6$ is not a C$_1$-C$_3$ alkyl;

(3) when at least one of $R^1$, $R^2$, $R^3$, and $R^4$ is not H, $R^5$ is —OH, $R^7$ is a bond, then $R^6$ is not a C$_1$-C$_4$ alkyl;

(4) when $R^1$, $R^2$, and $R^3$ are H, $R^4$ is —OCH$_3$, $R^5$ is —C(O)CH$_3$, and $R^6$ is a bond then $R^7$ is not a C$_3$alkyl; and (5) when $R^1$, $R^2$, $R^4$, and $R^5$ are H, $R^3$ is —OH, and $R^7$ is a bond then $R^6$ is not a methyl.

According one preferred embodiment, $R^1$ is hydrogen; $R^2$, $R^3$, and $R^4$ are independently hydrogen, halogen, —OH, or —OCH$_3$; $R^5$ is hydrogen, —OH, or —C(O)CH$_3$; $R^6$ is C$_1$-C$_{12}$ alkylene, and $R^7$ is a bond or para-phenylene. $R^7$ is more preferably a C$_7$-C$_9$ alkyl.

According to another preferred embodiment, at least one of $R^1$, $R^2$, $R^3$, and $R^4$ is hydrogen, —C(O)CH$_3$, —OH, Cl, —OCH$_3$, F, or —NO$_2$. In one more preferred embodiment, $R^2$ is —C(O)CH$_3$, —OH, —OCH$_3$, or —Cl. In another more preferred embodiment, $R^3$ is Cl, —OCH$_3$, F, or —OH. In yet another more preferred embodiment, $R^4$ is —OCH$_3$ or —NO$_2$.

According to yet another preferred embodiment, $R^5$ is —C(O)CH$_3$, —OH, H, —CH═CHCH$_3$, —NH$_2$, —NO$_2$, —NHC(O)CH$_3$, —CH═CHCO$_2$H, —C(O)CH$_2$CH$_3$, —C(O)NH$_2$, —C(O)NHCH$_3$, —COOH, —C(O)NHCH$_2$CH$_3$, —C(O)NHCH(CH$_3$)$_2$, —OCH$_3$, —C(CH$_3$)$_2$OH, —C(OH)(CH$_3$)$_2$, or —CH(OH)CH$_3$.

According to yet another preferred embodiment, $R^6$ is a linear C$_1$-C$_{12}$ alkylene. More preferably, $R^6$ is —(CH$_2$)$_n$—, where n is an integer from 1 to 10.

According to yet another preferred embodiment, $R^4$ and $R^5$ are not alkyl or halogen.

According to yet another preferred embodiment, $R^7$ is para-phenylene or a bond.

According to yet another preferred embodiment, $R^6$ is —CH$_2$— and $R^7$ is phenylene and, more preferably para-phenylene. More preferably, at least one of $R^1$, $R^2$, $R^3$, and $R^4$ is hydrogen. More preferably, $R^5$ is —C(O)CH$_3$, —OH or —C(CH$_3$)$_2$OH.

According to yet another preferred embodiment, $R^7$ is a bond, $R^5$ is —OH, and $R^1$, $R^2$, $R^3$, and $R^4$ are hydrogen. $R^6$ is preferably C$_4$-C$_{12}$ alkylene and, more preferably, C$_4$-C$_9$ alkylene.

According to yet another preferred embodiment, $R^7$ is a bond, $R^5$ is —OH, and at least one of $R^1$, $R^2$, $R^3$, and $R^4$ is not hydrogen. $R^6$ is preferably C$_1$-C$_{12}$ alkylene, more preferably C$_5$-C$_{12}$ alkylene, and most preferably C$_5$-C$_9$ alkylene.

According to yet another preferred embodiment, $R^7$ is a bond, $R^5$ is —C(O)CH$_3$, and $R^1$, $R^2$, $R^3$, and $R^4$ are hydrogen. $R^6$ is preferably C$_1$-C$_{12}$ alkylene, more preferably C$_3$-C$_{12}$ alkylene, and most preferably C$_3$-C$_7$ alkylene.

According to yet another preferred embodiment, $R^7$ is a bond and $R^1$, $R^2$, $R^3$, $R^4$ and $R^5$ are hydrogen. Preferably, $R^6$ is C$_7$-C$_8$ alkylene.

According to yet another preferred embodiment, $R^7$ is a bond, $R^5$ is hydrogen, and at least one $R^1$, $R^2$, $R^3$, and $R^4$ are not hydrogen. $R^6$ is preferably C$_1$-C$_{12}$ alkylene, more preferably C$_4$-C$_9$ alkylene, and most preferably C$_7$-C$_8$ alkylene.

According to yet another preferred embodiment, $R^2$ is —OH. More preferably, $R^7$ is a bond and $R^5$ is hydrogen. Preferably, $R^6$ is C$_1$-C$_{12}$ alkylene, more preferably C$_3$-C$_9$ alkylene, and most preferably C$_7$ alkylene.

According to yet another preferred embodiment, $R^3$ is —OH. More preferably, $R^7$ is a bond and $R^5$ is hydrogen. $R^6$ is preferably C$_1$-C$_{12}$ alkylene, more preferably C$_3$-C$_9$ alkylene, and most preferably C$_7$ alkylene.

Other suitable delivery agents include those having the following structure and pharmaceutically acceptable salts thereof:

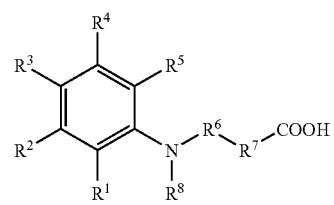

Formula (6)

wherein $R^1$, $R^2$, $R^3$, and $R^4$ are independently H, —OH, halogen, —OCH$_3$, —NR$^{10}$R$^{11}$ or —N$^+$R$^{10}$R$^{11}$R$^{12}$(R$^{13}$)$^-$;

$R^5$ is H, —OH, —NO$_2$, —NR$^{14}$R$^{15}$, —N$^+$R$^{14}$R$^{15}$R$^{16}$ (R$^{13}$)$^-$, amide, C$_1$-C$_{12}$ alkoxy, C$_1$-C$_{12}$ alkyl, C$_2$-C$_{12}$ alkenyl, carbamate, carbonate, urea, or —C(O)R$^{18}$;

$R^5$ is optionally substituted with —OH, —SH, or —COOH;

$R^5$ is optionally interrupted by O, N, S, or —C(O)—;

$R^6$ is a C$_1$-C$_{12}$ alkylene, C$_1$-C$_{12}$ alkenylene, or arylene;

$R^6$ is optionally substituted with a C$_1$-C$_4$ alkyl, C$_2$-C$_4$ alkenyl, C$_1$-C$_4$ alkoxy, —OH, —SH, halogen, —NH$_2$, or —CO$_2$R$^9$;

$R^6$ is optionally interrupted by O or N;

$R^7$ is a bond or arylene;

$R^7$ is optionally substituted with —OH, halogen, —C(O)CH$_3$, —NR$^{10}$R$^{11}$ or —N$^+$R$^{10}$R$^{11}$R$^{12}$ (R$^{13}$)$^-$;

$R^8$ is H or C$_1$-C$_4$ alkyl;

$R^9$ is H, C$_1$-C$_4$ alkyl, or C$_2$-C$_4$ alkenyl;

$R^{10}$, $R^{11}$, and $R^{12}$ are independently H or C$_1$-C$_{10}$ alkyl;

$R^{13}$ is a halide, hydroxide, sulfate, tetrafluoroborate, or phosphate;

$R^{14}$, $R^{15}$, and $R^{16}$ are independently H, C$_1$-C$_{10}$ alkyl, C$_2$-C$_{12}$ alkenyl, O, or —C(O)R$^{17}$;

$R^{17}$ is —OH, C$_1$-C$_{10}$ alkyl, or C$_2$-C$_{12}$ alkenyl; and $R^{18}$ is —OH, $C_1$-$C_6$ alkyl, —$NR^{14}R^{15}$, —$N^+R^{14}R^{15}R^{16}$ ($R^{13}$)⁻.

According to one embodiment, when $R^5$ is $OCH_3$ then $R^6$ is $C_1$-$C_8$ or $C_{10}$-$C_{12}$ alkyl.

According to a preferred embodiment, $R^5$ is not —$OCH_3$. More preferably, $R^5$ is not alkoxy.

According to another preferred embodiment, $R^1$, $R^2$, $R^3$, and $R^4$ are hydrogen, $R^5$ is —COOH, —$C(O)NH_2$, —$C(O)CH_3$, or —$NO_2$, $R^6$ is —$(CH_2)_7$—, and $R^7$ is a bond.

According to yet another preferred embodiment, $R^1$, $R^2$, $R^3$, and $R^4$ are hydrogen, $R^5$ is —$C(O)NH_2$, $R^6$ is —$CH_2$—, and $R^7$ is a para-phenylene.

According to one embodiment, the delivery agents of formula (6) have the formula:

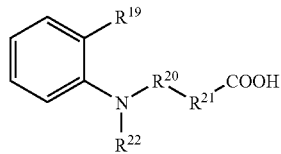

Formula (7)

wherein
$R^{19}$ is —$NO_2$ or —$C(O)R^{23}$;
$R^{20}$ is a $C_1$-$C_{12}$ alkylene or $C_1$-$C_{12}$ alkenylene;
$R^{21}$ is a bond or arylene;
$R^{22}$ is H or $C_1$-$C_4$ alkyl; and
$R^{23}$ is —OH, $C_1$-$C_6$ alkyl, or —$NH_2$.

Preferred delivery agents include, but are not limited to, SNAC, SNAD, 8-(N-2-hydroxy-5-chlorobenzoyl)aminocaprylic acid, 8-(N-2-hydroxy-4-methoxybenzoyl)-amino-caprylic acid, 4-CNAB, and pharmaceutically acceptable salts thereof.

According to one preferred embodiment, the delivery agent is SNAC or a pharmaceutically acceptable salt thereof. In one embodiment, the delivery agent is a sodium salt of SNAC. In another embodiment, the delivery agent is the monosodium salt of SNAC and can be, for example, any of the polymorphic forms of monosodium SNAC disclosed in U.S. Provisional Application No. 60/569,476, filed May 6, 2004, and U.S. Provisional Application No. 60/619,418, filed Oct. 15, 2004, both of which are hereby incorporated by reference. In yet another embodiment, the delivery agent is the disodium salt of SNAC.

According to another preferred embodiment, the delivery agent is SNAD or a pharmaceutically acceptable salt thereof. In one embodiment, the delivery agent is a sodium salt of SNAD. In another embodiment, the delivery agent is the disodium salt of SNAD.

According to yet another preferred embodiment, the delivery agent is 4-CNAB or a pharmaceutically acceptable salt thereof. In one embodiment, the delivery agent is a sodium salt of 4-CNAB. The sodium 4-CNAB can be any of the amorphous and polymorphic forms described in International Publication No. WO 03/057650, which is hereby incorporated by reference.

Other suitable delivery agents of the present invention are described in U.S. Pat. Nos. 6,699,467, 6,663,898, 6,693,208, 6,693,073, 6,693,898, 6,663,887, 6,646,162, 6,642,411, 6,627,228, 6,623,731, 6,610,329, 6,558,706, 6,525,020, 6,461,643, 6,461,545, 6,440,929, 6,428,780, 6,413,550, 6,399,798, 6,395,774, 6,391,303, 6,384,278, 6,375,983, 6,358,504, 6,346,242, 6,344,213, 6,331,318, 6,313,088, 6,245,359, 6,242,495, 6,221,367, 6,180,140, 6,100,298, 6,100,285, 6,099,856, 6,090,958, 6,084,112, 6,071,510, 6,060,513, 6,051,561, 6,051,258, 6,001,347, 5,990,166, 5,989,539, 5,976,569, 5,972,387, 5,965,121, 5,962,710, 5,958,451, 5,955,503, 5,939,381, 5,935,601, 5,879,681, 5,876,710, 5,866,536, 5,863,944, 5,840,340, 5,824,345, 5,820,881, 5,811,127, 5,804,688, 5,792,451, 5,776,888, 5,773,647, 5,766,633, 5,750,147, 5,714,167, 5,709,861, 5,693,338, 5,667,806, 5,650,386, 5,643,957, 5,629,020, 5,601,846, 5,578,323, 5,541,155, 5,540,939, 5,451,410, 5,447,728, 5,443,841, and 5,401,516. Delivery agents of the present invention are also described in U.S. Published Application Nos. 20040110839, 20040106825, 20040068013, 20040062773, 20040022856, 20030235612, 20030232085, 20030225300, 20030198658, 20030133953, 20030078302, 20030072740, 20030045579, 20030012817, 20030008900, 20020155993, 20020127202, 20020120009, 20020119910, 20020102286, 20020065255, 20020052422, 20020040061, 20020028250, 20020013497, 20020001591, 20010039258, and 20010003001. Delivery agents of the present invention are also described in International Publication Nos. WO 2004/104018, WO 2004080401, WO 2004062587, WO 2003/057650, WO 2003/057170, WO 2003/045331, WO 2003/045306, WO 2003/026582, WO 2002/100338, WO 2002/070438, WO 2002/069937, WO 02/20466, WO 02/19969, WO 02/16309, WO 02/15959, WO 02/02509, WO 01/92206, WO 01/70219, WO 01/51454, WO 01/44199, WO 01/34114, WO 01/32596, WO 01/32130, WO 00/07979, WO 00/06534, WO 00/06184, WO 00/59863, WO 00/59480, WO 00/50386, WO 00/48589, WO 00/47188, WO 00/46182, WO 00/40203, WO 99/16427, WO 98/50341, WO 98/49135, WO 98/34632, WO 98/25589, WO 98/21951, WO 97/47288, WO 97/31938, WO 97/10197, WO 96/40076, WO 96/40070, WO 96/39835, WO 96/33699, WO 96/30036, WO 96/21464, WO 96/12475, and WO 9612474. Each of the above listed U.S. patents and U.S. and International published applications are herein incorporated by reference.

The delivery agent compounds depicted as carboxylic acids may be in the form of the carboxylic acid or salts thereof. Suitable salts include, but are not limited to, organic and inorganic salts, for example alkali-metal salts, such as sodium (e.g., monosodium and disodium salts), potassium and lithium; alkaline-earth metal salts, such as magnesium, calcium or barium; ammonium salts; basic amino acids, such as lysine or arginine; and organic amines, such as dimethylamine or pyridine. Preferably, the salts are sodium salts. The salts may be mono- or multi-valent salts, such as monosodium salts and di-sodium salts. The salts may also be solvates, including ethanol solvates, and hydrates.

The delivery agent compounds depicted as amines may be in the form of the free amine or salts thereof. Suitable salts include, but are not limited to, organic and inorganic salts, for example sodium salts, sulfate salts, hydrochloride salts, phosphate salts, fluoride salts, carbonate salts, tartrate salts, oxalates, oxides, formates, acetate or citrate.

Salts of the delivery agent compounds of the present invention may be prepared by methods known in the art. For example, sodium salts may be prepared by dissolving the delivery agent compound in ethanol and adding aqueous sodium hydroxide.

Where the delivery agent has an amine moiety and a carboxylic acid moiety, poly amino acids and peptides comprising one or more of these compounds may be used. An amino acid is any carboxylic acid having at least one free amine group and includes naturally occurring and synthetic amino acids. Poly amino acids are either peptides (which are two or more amino acids joined by a peptide bond) or are two or more amino acids linked by a bond formed by other groups which can be linked by, e.g., an ester or an anhydride linkage.

Peptides can vary in length from dipeptides with two amino acids to polypeptides with several hundred amino acids. One or more of the amino acids or peptide units may be acylated or sulfonated.

The delivery agent may contain a polymer conjugated to it such as described in International Publication No. WO 03/045306. For example, the delivery agent and polymer may be conjugated by a linkage group selected from the group consisting of —NHC(O)NH—, —C(O)NH—, —NHC(O), —OOC—, —COO—, —NHC(O)O—, —OC(O)NH—, —CH₂NH—NHCH₂—, —CH₂NHC(O)O—, —OC(O)NHCH₂—, —CH₂NHCOCH₂O—, —OCH₂C(O)NHCH₂—, —NHC(O)CH₂O—, —OCH₂C(O)NH—, —NH—, —O—, and carbon-carbon bond, with the proviso that the polymeric delivery agent is not a polypeptide or polyamino acid. The polymer may be any polymer including, but not limited to, alternating copolymers, block copolymers and random copolymers, which are safe for use in mammals.

Preferred polymers include, but are not limited to, polyethylene; polyacrylates; polymethacrylates; poly(oxyethylene); poly(propylene); polypropylene glycol; polyethylene glycol (PEG); and derivatives thereof and combinations thereof. The molecular weight of the polymer typically ranges from about 100 to about 200,000 daltons. The molecular weight of the polymer preferably ranges from about 200 to about 10,000 daltons. In one embodiment, the molecular weight of the polymer ranges from about 200 to about 600 daltons and more preferably ranges from about 300 to about 550 daltons.

The compounds described herein may be derived from amino acids and can be readily prepared from amino acids by methods within the skill of those in the art, such as those described in International Publication Nos. WO96/30036, WO97/36480, WO00/06534, WO00/46812, WO00/50386, WO00/59863, WO 01/32596, and WO 00/07979 and U.S. Pat. Nos. 5,643,957, 5,650,386, and 5,866,536, all of which are incorporated by reference. For example, the compounds may be prepared by reacting the single amino acid with the appropriate acylating or amine-modifying agent, which reacts with a free amino moiety present in the amino acid to form amides. Protecting groups may be used to avoid unwanted side reactions as would be known to those skilled in the art. With regard to protecting groups, reference is made to T. W. Greene, *Protecting Groups in Organic Synthesis*, Wiley, New York (1981), the disclosure of which is hereby incorporated herein by reference.

The delivery agent compound may be purified by recrystallization or by fractionation on one or more solid chromatographic supports, alone or linked in tandem. Suitable recrystallization solvent systems include, but are not limited to, acetonitrile, methanol, ethanol, ethyl acetate, heptane, water, tetrahydrofuran, and combinations thereof. Fractionation may be performed on a suitable chromatographic support such as alumina, using methanol/n-propanol mixtures as the mobile phase; reverse phase chromatography using trifluoroacetic acid/acetonitrile mixtures as the mobile phase; and ion exchange chromatography using water or an appropriate buffer as the mobile phase. When anion exchange chromatography is performed, preferably a 0-500 mM sodium chloride gradient is employed.

Gallium Salts and Complexes

Gallium salts which may be employed are those which are pharmaceutically acceptable including nitrate, maltolate, citrate, halide (preferably chloride), carbonate, acetate, triacetate, tartrate, oxalate, oxide, hydroxide and hydrated oxide as well as those described in U.S. Pat. Nos. 4,529,593, and 4,704,277, which are hereby incorporated by reference. Generally, these gallium salts are non-radioactive. Preferred gallium salts include, but are not limited to, gallium chloride and gallium nitrate and hydrates thereof, such as gallium nitrate nonahydrate.

Gallium complexes which may be employed include those described in U.S. Pat. Nos. 5,258,376, 5,574,027, 5,883,088, 5,968,922, 5,981,518, 5,998,397, 6,004,951, 6,048,851, and 6,087,354, as well as those described in Finnegan et al. Inorganic Chemistry, 26:2171-2176 (1987) and Farrar et al., Food and Chemical Toxicology, 26:523-525 (1988). Each of these references are hereby incorporated by reference. For example, gallium chelates and complexes of 3-hydroxy-4-pyrones (such as a complex of maltol) may be used.

In one embodiment, the gallium complex in the pharmaceutical formulation is a neutral 3:1 (hydroxypyrone:gallium) complex, in which the hydroxypyrone is either an unsubstituted 3-hydroxy-4-pyrone (pyromeconic acid) or a 3-hydroxy-4-pyrone substituted with one to three lower alkyl substitutents (including methyl, ethyl, isopropyl, and n-propyl groups). In a still further embodiment, the 3-hydroxy-4-pyrone is 3-hydroxy-4-pyrone, 3-hydroxy-2-methyl-4-pyrone, 3-hydroxy-2-ethyl-4-pyrone, and 3-hydroxy-6-methyl-4-pyrone. The amount of the hydroxypyrone:gallium complex in the dosage form can be, for example, 0.9 to 1800 mg or 9 to 360 mg.

In another embodiment, the gallium complex in the pharmaceutical formulation is a neutral 3:1 (hydroxypyrone:gallium) complex, and the hydroxypyrone has the formula:

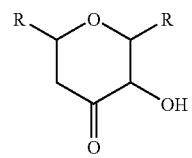

wherein each R is independently selected from hydrogen and alkyl of from 1 to 6 carbon atoms. In a still further embodiment, R is acyclic and unbranched. The hydroxypyrone in the gallium complex can be, for example, maltol or pyromeconic acid. According to one embodiment, the complex is gallium maltolate (tris(3-hydroxy-2-methyl-4H-pyran-4-onato)gallium). See Bernstein et al., "Chemistry and Pharmacokinetics of Gallium Maltolate. A Compound With High Oral Gallium Bioavailability", *Metal-Based Drugs* 7(1):33-47 (2000), which is hereby incorporated by reference.

The aforementioned gallium hydroxypryone complex can be administered with a pharmaceutically compatible buffering agent to raise the pH of the stomach fluids to about 5-9, and preferably to about 6-7. Examples of such buffering agents include, but are not limited to, calcium carbonate (CaCO₃), and sodium bicarbonate (NaHCO₃). In one embodiment, the gallium complex is administered with calcium carbonate, sodium bicarbonate, and/or an excess of free hydroxypyrone (or a salt thereof containing a physiologically acceptable cation). The weight ratio of free hydroxypyrone to gallium complex preferably ranges from 0.1 to 100. In one embodiment, the gallium complex is administered in a delayed release form with or without calcium carbonate, sodium bicarbonate, and/or an excess of free hydroxypyrone (or a salt thereof containing a physiologically acceptable cation). The buffering agent and/or free hydroxypyrone can be included in the pharmaceutical formulation of the present invention, or administered concurrently therewith.

In another embodiment, gallium is administered as a complex having the formula:

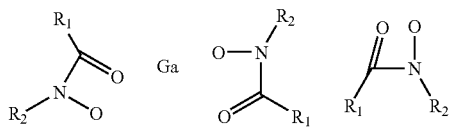

wherein each occurrence of $R_1$ is a $C_1$-$C_8$ n-alkyl and each occurrence of $R_2$ is H or $C_1$-$C_2$ alkyl, or $R_1$ and $R_2$ together from tetra or penta-methylene. See U.S. Pat. No. 5,196,412, which is hereby incorporated by reference.

According to another embodiment, the pharmaceutical formulation includes from about 0.01, 0.1, or 0.5 to about 1, 5, 10, or 20 grams of gallium salt. According to yet another embodiment, the pharmaceutical formulation includes a sufficient amount of gallium salt to provide, upon ingestion to a human, from about 10 to about 400 or 1400 mg/m²/day or more preferably 100-300 mg/m²/day. When treating hypercalcemia, this dose can be continued for about five days, or can be discontinued if optimum serum calcium concentrations are attained in less than five days. According to yet another embodiment, the pharmaceutical formulation includes a sufficient amount of gallium salt to provide, upon ingestion to a human, one or more of the following: (a) plasma gallium concentrations of about 0.1 to about 5 µg/ml or about 0.9 to about 2.0 µg/ml, (b) average steady state plasma levels of gallium from about 1000 to about 2500 ng/ml, or (c) a decrease in serum ionized calcium (corrected for albumin) of at least 2.0 mg/dl in a human with hypercalcemia (such as cancer-related hypercalcemia).

Formulation Techniques for Preparing Stable Pharmaceutical Formulations Containing Gallium Salts and Delivery Agent Compounds An embodiment of the invention provides pharmaceutical formulations that address stability problems associated with oral formulations of gallium salts, especially gallium nitrate and delivery agent compounds. A major problem encountered with the development of oral formulations of gallium salts is an oxidation reaction that occurs in the presence of gallium nitrate and the delivery agent compound. The presence of water and trace amounts of nitric acid both associated with the gallium nitrate are believed to contribute to the oxidation reaction. Oxidation reactions, evidenced by brown discoloration of the dosage form, results in a delivery agent and/or gallium salt degradation product, which is not desired. For example, the conversion of gallium nitrate to poorly soluble gallium oxide or gallium hydroxide degradation products impairs the absorption of the gallium molecule.

While not being bound to any particular theory, it is believed that the interaction between gallium nitrate and delivery agent compounds, along with the presence of water and/or nitric acid causes, or at least facilitates an oxidation reaction that yields degradation products and discolors the dosage form. It is also believed that delivery agent compounds with phenolic rings are more prone to such oxidation reactions. As such, oxidation can be reduced or completely suppressed by reducing the proximity of gallium nitrate and the delivery agent compound, i.e. reducing the number of very close contact points that can occur during formulation processing. Also oxidation may be suppressed if water associated with the gallium salt is sequestered upon release via, for example, use of water-absorbing excipients and/or gentle drying. Also neutralizing the trace amounts of nitric acid associated with the gallium nitrate may suppress the oxidation reaction.

One embodiment of the invention provides a method of preparing a pharmaceutical composition comprising a gallium salt and a delivery agent compound which includes the step of introducing the gallium salt prior to introducing the delivery agent compound (e.g. SNAD). The gallium salt is mixed with formulating materials such as diluents, compression aids or anti-oxidants prior to the addition of the delivery agent compound to the formulation thereby insulating the gallium nitrate and minimizing the interaction between the gallium salt and the delivery agent compound. Alternatively, the order may be reversed—delivery agent may be added first, "insulating" excipients then added, followed by addition of the gallium salt. Preventing close interaction between the gallium salt and the delivery agent compound (particularly during compression) seeks to hinder or suppress an oxidation reaction.

Another embodiment of this invention provides a method of preparing a pharmaceutical composition comprising a gallium salt and a delivery agent compound which includes the step of separately preparing delivery agent granules and gallium salt granules. One set of granules consists essentially of a delivery agent and intragranular excipients (if any), the second set of granules consists essentially of a gallium salt and intragranular excipients. A preferred embodiment involves preparing granules of gallium nitrate and granules of SNAD and then mixing the separately formed granules and later compressing the two sets of granules into tablets or filling capsules with the two sets of granules. Viscosity increasing excipients may be further included in the formulation for oral administration.

Yet another embodiment of the invention provides a method of preparing a pharmaceutical composition comprising a delivery agent compound and/or a gallium salt which includes the step of dissolving a gallium salt (e.g. gallium nitrate) in water, optionally followed by neutralization of any nitric acid in association with the gallium nitrate. In one application of this embodiment, the gallium nitrate solution is then used as the granulating solution for granulating SNAD (or another delivery agent) and/or other excipients in the formulation to form granules that are further processed into tablets or capsules. Methods of neutralization include raising the pH of the gallium nitrate solution to about 7-7.5 by addition of a base (e.g. sodium citrate, sodium acetate, potassium acetate or sodium hydroxide), or addition of a base to the admixture to which the aqueous gallium nitrate granulating fluid is added.

The gallium nitrate formulations may be processed as described in the above paragraph except that a delivery agent compound is not added to the formulation. Preferably, however, the formulations contain a delivery agent compound.

Alternatively, the gallium nitrate solution in which the nitric acid has been neutralized can be dried to form granules consisting essentially of gallium nitrate and intragranular excipients (if any), i.e. granules without a delivery agent compound. In a preferred embodiment, the granules consisting essentially of gallium nitrate may be subsequently mixed with granules consisting essentially of delivery agent compound (e.g. SNAD). In either embodiment, antioxidants and binders can be added to the gallium nitrate solution.

One embodiment of the invention provides a method of preparing a pharmaceutical composition comprising a gallium salt and a delivery agent compound which includes a low-shear mixing technique or a low-shear granulating technique for the powder blends of gallium salt (e.g. gallium nitrate) and delivery agent compound (e.g. SNAD). The low-shear mixing or granulating technique limits the extent of gallium salt/delivery agent particle-particle interaction and also reduces the release of water associated with the gallium salt. This seeks to limit or completely suppress the oxidation reaction. In one embodiment, the low-shear mixing technique occurs in a mixer/granulator using a rotary speed of 30-500 rpm, preferably 30-300 rpm or 30-100 rpm. Low shear mixing or granulating can be carried out using commercially available low shear mixers/granulators, for example, using a KitchenAid® Mixer, Chemineer® Nimix Mixing System or a Hobart® mixer. Low-shear mixing or granulating techniques also include use of commercially available tumbler blenders that mix with a gentle rolling action, including ribbon blenders and V-shaped blenders (e.g., a V-shaped blender with a liquid addition system).

Another embodiment of the invention provides a method of preparing a pharmaceutical composition comprising a gallium salt and a delivery agent compound which includes the step of gently drying wet granules. Generally, drying occurs around 60-70° C. and, depending on the application, may occur for less than 2 hours in duration. In contrast, embodiments of the present invention employ drying over longer periods of time at lower temperatures, i.e. embodiments of the present invention employ a gentle drying technique. Preferably drying occurs at a temperature range of 30-50° C., more preferably 30-40° C., over a period of 2-12 hours, preferably 4-12 hours. The use of the gentle drying technique reduces the availability of water associated with the gallium nitrate to contribute to the oxidation reaction.

Another embodiment of the invention provides a method of preparing a pharmaceutical composition comprising a gallium salt and a delivery agent compound which includes the step of using low compression pressures to obtain tablets. In one embodiment, compression pressures of less than about 1500 psi are employed, preferably less than about 800 psi. In one embodiment the product is not compressed, and the unit dosage is in the form of a powder (e.g. a powder pack). Introduction of compression aids, including but not limited to, colloidal silica and microcrystalline cellulose, facilitate the compression of powders or granules into a tablet at lower pressures than otherwise required without the compression aid.

Any one of the above-described processing techniques may be combined with one or more of the other above-described processing techniques to provide stable pharmaceutical compositions containing a gallium salt and a delivery agent compound. In a preferred application of any one of these embodiments, the gallium salt is gallium nitrate (e.g., gallium nitrate nonahydrate) and the delivery agent compound is SNAD, including the disodium salt of SNAD.

In addition to providing stability, the above processing techniques themselves may increase the bioavailability of gallium salts upon being orally administered. In one embodiment, the above processing techniques are performed without the addition of a delivery agent compound. Because the delivery agent compound also facilitates the oral bioavailability of the gallium salt, preferred embodiments include delivery agent compounds.

Stable Pharmaceutical Formulations Containing Gallium Salts and a Delivery Agent Compound Another aspect of the present invention provides stable pharmaceutical formulations containing a gallium salt and a delivery agent compound. These formulations are preferably prepared by the methods described above, or they may be prepared by other methods known in the art, including but not limited to, preparation of powder blends, process of wet granulation, drying of wet granules, preparation of powder blends for direct compression or any combination thereof.

One embodiment of this invention provides a pharmaceutical composition that includes a gallium salt and a delivery agent compound that further contains an amount of excipient sufficient to dilute the gallium salt and nitric acid and water associated therewith and thus limit any oxidization reaction with the delivery agent compound (e.g. SNAD). As used herein, excipients include diluents, binding agents, compression aids, highly porous agents, absorbent agents, hydrophilic polymers, dessicants, compressibility aids, antioxidant agents and disintegrants. Non-limiting examples of excipients include: croscarmellose sodium (e.g. 0.5-50% w/w), polyvinyl pyrollidone (e.g. 0.2-50% w/w), and crospovidone (e.g. 0.5-50% w/w), talc, and magnesium stearate. Also, the inclusion of excipients containing other metals such as sodium and potassium (e.g. sodium or potassium citrate) (e.g. 0.5-50% w/w) may prevent the production of gallium hydroxide from gallium nitrate.

In one embodiment of the invention, the amount of excipients in the pharmaceutical composition is from about 0.2% or 2% to about 65% or 75% (w/w), based on the total weight of the pharmaceutical composition. In one embodiment of the invention, the amount of excipients present in the pharmaceutical compositions exceeds that which is conventionally found in unit dosage forms. For example, in embodiments of the invention the amount of excipients in the pharmaceutical composition may range from about 55% or 60% to about 65% or 75% (w/w), based on the total weight of the pharmaceutical composition. This has the beneficial effect of diluting the trace amounts of nitric acid associated with gallium nitrate and limits the nitric acid reaction or interaction with the delivery agent compound and gallium salt.

Another embodiment of this invention provides pharmaceutical compositions containing a gallium salt and a delivery agent compound that further includes highly porous and/or absorbent agents (e.g. hydrophilic agents). These agents can: (1) imbibe the water in gallium formulations, thus minimizing its availability for reaction; and (2) serve as inert templates that will stabilize the mixture of a delivery agent compound and a gallium salt. Examples include, but are not limited to starch (e.g. 2-75% w/w), silicas such as colloidal silica (e.g. 1-20% w/w); celluloses such as silicified microcrystalline cellulose (e.g. 2-75% w/w), microcrystalline cellulose (e.g. 2-75% w/w), kaolinite (aluminum silicate hydroxide, e.g. 1-50% w/w), alumina (e.g. 1-50% w/w), and magnesium aluminum silicate (e.g. 1-10% w/w). Another example of absorbent agents that can be added are gelatins, such as low molecular weight gelatin (e.g. 1-50% w/w), including those that can adsorb water up to about 10% of its weight. Further examples include hydrophilic polymers such as, but not limited to, hydroxylpropyl methyl cellulose (1-50% w/w) and sodium alginate (1-50% w/w).

Yet another embodiment of this invention provides a pharmaceutical composition that includes a gallium salt and a delivery agent compound that further includes compression aids including but not limited to microcrystalline cellulose (e.g. 1-75% w/w), anhydrous lactose (e.g. 1-75% w/w) and spray dried lactose (e.g., 1-75% w/w). Such compression aids facilitate the compression of gallium nitrate and delivery agent compound at lower pressures. Further these compression aids act as excipients to dilute the gallium salt and associated nitric acid and water and thus limit any oxidization reaction with the delivery agent compound (e.g. SNAD).

Yet another embodiment of this invention provides a pharmaceutical composition that includes a gallium salt and a delivery agent compound that further includes an antioxidant agent to prevent or inhibit potential oxidation reaction. Non-limiting examples of antioxidant agents include, but are not limited to, propyl gallate, ascorbates, alpha tocopherol, and vitamin C. In one embodiment of the present invention, the pharmaceutical composition contains from about 0.2% or 1% to about 20% or 25% (w/w) of antioxidants, based on the total weight of the pharmaceutical composition.

Yet another embodiment of the invention provides a pharmaceutical composition that includes a gallium salt and a delivery agent compound that further includes a desiccant. The tablet can be incorporated into the tablet, such as tablets coated with a moisture proofing coat to ensure long-term stability, or the packaging or container of the pharmaceutical composition may contain dessicants to prevent the addition and accumulations of moisture. The resulting dosage form can also be packaged in a container with low moisture vapor transmission.

Any of the above-described pharmaceutical formulation may be a sustained release oral pharmaceutical formulation which provides for controlled, modified, delayed and/or sustained release of the gallium salt. Such formulations can be prepared by methods known in the art. Examples include but are not limited to: (i) preparation of double-layered tablets that will contain a fast—release layer and a controlled-release layer; (ii) application of various polymers or excipients applied either alone or in suitable combinations such as various grades of hydroxyl propyl methyl cellulose; hydroxyl ethyl cellulose, sodium alginate and microcrystalline cellulose, gelatin and algnic acid. Because the anticalcium effect of gallium salts is schedule related (i.e., prolonged exposure to lower concentrations produces greater inhibition of bone resorption than short treatment with high doses), the sustained release oral formulations of the present invention may provide improved efficacy. Sustained release formulations may also reduce undesirable side effects resulting from rapid absorption of the gallium salt, such as nausea, vomiting, and an increased risk of renal insufficiency.

To improve bioavailability, the gallium salt particles and/or the delivery agent particles are in a micronized form. The particles can be in the form of fine granules or micro-beads and may have a median size of less than 900 or 1000 µm. For example, the median particle size can range from about 45 to about 840 µm, from about 45 to about 150 µm, from about 150 to about 250 µm, from about 250 to about 425 µm, from about 425 to about 850 µm, from about 100 to about 1000 µm and from about 500 to about 1000 µm. According to another embodiment, the particles have a median particle size less than about 1 µm. In one embodiment, only the delivery agent is in micronized form. In another embodiment, both the delivery agent and gallium salt is in micronized form. Gallium nitrate and/or delivery agent (e.g., SNAD) can be dosed as a capsule or tablet in fast release or delayed release formulations. Such formulations can also contain, for example, chitosan, alginic acid, dextrans, gelatin and polymethacrylic acid. Methods of preparing micronized particles are disclosed in U.S. Ser. No. 11/204,778, filed Sep. 6, 2005, which is hereby incorporated by reference in its entirety.

Solid pharmaceutical formulations may be in the form of tablets, capsules (including hard and soft gelatin capsules), and particles, such as powders and sachets. In one embodiment of the present invention, the pharmaceutical composition is in the form of a powder to avoid oxidation problems sometimes observed when the powder is compressed into a tablet. Solid dosage forms may be prepared by mixing the solid form of the delivery agent with the solid form of the gallium salt. Alternately, a solid may be obtained from a solution of delivery agent and gallium salt by methods known in the art, such as freeze-drying (lyophilization), precipitation, crystallization and solid dispersion.

The pharmaceutical formulations of the present invention can also include one or more enzyme inhibitors. Such enzyme inhibitors include, but are not limited to, compounds such as actinonin or epiactinonin and derivatives thereof. Other enzyme inhibitors include, but are not limited to, aprotinin (Trasylol) and Bowman-Birk inhibitor.

The pharmaceutical formulations can also include any one or combination of plasticizers, colorants, flavorants, taste-masking agents, sugars, sweeteners, salts, and dosing vehicles, including, but not limited to, water, 1,2-propane diol, ethanol, olive oil, or any combination thereof.

The amount of gallium salt (e.g., gallium nitrate) included in the pharmaceutical formulation is an amount effective to accomplish the purpose of the gallium containing salt for the target indication. The amount of gallium salt in the pharmaceutical formulation typically is a pharmacologically, biologically, therapeutically, or chemically effective amount. However, the amount can be less than that amount when the pharmaceutical formulation is used in a dosage unit form of the present invention because the dosage unit form may contain a plurality of delivery agent/gallium salt pharmaceutical formulations or may contain a divided pharmacologically, biologically, therapeutically, or chemically effective amount. The total effective amount can then be administered in cumulative units containing, in total, an effective amount of the gallium salt.

The total amount of gallium salt to be used can be determined by methods known to those skilled in the art. However, because the pharmaceutical formulations of the invention may deliver gallium salt more efficiently than formulations containing the gallium salt alone, lower amounts of gallium salt than those used in prior dosage unit forms or delivery systems can be administered to the subject, while still achieving the same blood levels and therapeutic effects.

The delivery agents facilitate the delivery of gallium salt, particularly in oral form, but are also be useful in intranasal, sublingual, intraduodenal, subcutaneous, buccal, intracolonic, rectal, vaginal, mucosal, pulmonary, transdermal, intradermal, parenteral, intravenous, intramuscular and ocular systems.

The pharmaceutical formulations are useful for administering gallium salts to mammals including, but not limited to, horses, rodents, cows, pigs, dogs, cats, primates, and particularly humans.

According to another embodiment the pharmaceutical formulation includes other medications which treat, cure, mitigate or prevent hypercalcemia, malignancies, or other indications for which gallium is effective. For example, in one embodiment, the pharmaceutical composition includes a chemotherapeutic agent. In another embodiment, the pharmaceutical composition includes an adjunctive chemotherapeutic agent. The pharmaceutical formulation of the present invention may be administered during or subsequent to chemotherapy. According to one preferred embodiment, when the pharmaceutical formulation is to be administered subsequent to chemotherapy, the pharmaceutical formulation includes an adjunctive chemotherapeutic agent, such as filgrastim or erythropoietin.

Methods of Treatment

The pharmaceutical formulation of the present invention can be administered to treat and/or prevent any disorder for which gallium salts are known to be capable of treating and/or preventing. Typically, an effective amount of the pharmaceutical formulation is administered to treat and/or prevent the desired disorder. Such disorders include, but are not limited to, hypercalcemia (including cancer-related hypercalcemia and hypercalcemia associated with malignancies, including non-small cell lung cancer, breast cancer, prostate cancer, multiple myeloma, squamous cell cancers, kidney cancer, uretral and bladder cancers, and cancers of head and neck), a disorder associated with excessive (or accelerated) loss of calcium from bone, osteopenia, osteoporosis, bone destruction due to metastasis from malignant tumors, hyperparathyroidism, and periodontal disease.

The pharmaceutical formulation can also be administered to:

(1) increase uptake of calcium by bones bone in a mammal (such as a human), inhibit resorption (or release) of calcium from bone in a mammal (such as a human) with hypercalcemia, bone fragility, or other disorders associated with abnormally increased calcium resorption (or release), (2) treat bone pain due to excessive (or accelerated) loss of calcium from bone, and/or (3) prevent bone fractures due to excessive (or accelerated) loss of calcium from bone, (4) treat or prevent Paget's disease, (5) inhibit osteoclastic activity, and/or promote osteoblastic activity, (6) treat or prevent of urethral (urinary tract) malignancies, (7) treat or prevent tumors, (8) treat or prevent cancers, including urethral, small cell lung, genitourinary malignancies such as prostrate, testicular and bladder cancers, lymphoma, leukemia, and multiple myeloma, (9) manage bone metastases (and associated pain),

(10) attenuate immune response, including allogenic transplant rejection,

(11) disrupt iron metabolism,

(12) promote cell migration,

(13) enhance repair and augmentation of skin, and connective and support tissues (e.g. skin, tendon, fascia, collagen-containing tissue than encapsulate tissue, bone), i.e. wound repair,

(14) attenuate, treat, or prevent infectious processes of *Mycobacterium* species, including but not limited to, *Mycobacterium tuberculosis*, and *Mycobacterium avium* complex,

(15) treat skin disorders and blemishes, e.g., facilitate healing of tears, breaks, wrinkles or defects in the skin,

(16) treat AIDS-associated non-Hodgkin's lymphoma (see U.S. Pat. No. 6,562,870),

(17) treat viral infections, e.g. to treat HIV (see U.S. Pat. No. 5,525,598), and

(18) increase bone growth, decrease hydroxyapatite solubility, increase the size and/or the perfection of hydroxyapatite crystals in bone, and/or increase the tensile strength of bone,

(19) increase calcium accretion in bone tissue and/or decrease bone resorption, and

(20) treat or prevent urothelial carcinoma or nonsquamous cell cervical carcinoma (see Bernstein et al., *Metal-Based Drugs* 7(1):33-47 (2000)).

The pharmaceutical formulations can be administered to treat the indications for gallium salts found in (1) the *Physicians' Desk Reference* (58$^{th}$ Ed., 2004, Medical Economics Company, Inc., Montvale, N.J.), (2) Fauci, A S, et. al., *Harrison's Principles of Internal Medicine* (14$^{th}$ Ed., 1998, McGraw-Hill Health Professions Division, New York), and (3) U.S. Pat. Nos. 4,529,593, 4,704,277, 5,196,412, 5,258, 376, 5,525,598, 5,556,645, 5,574,027, 5,686,116, 5,883,088, 5,981,518, 5,998,397, 5,968,922, 6,004,951, 6,048,851, 6,087,354, 6,165,514, and 6,562,870. All of the above-mentioned patents and publications are herein incorporated by reference in their entirety.

Cancer-related hypercalcemia can be treated by administration of the pharmaceutical formulation of the present invention containing a relatively high dose of a gallium salt for several days, followed by daily administration of a pharmaceutical formulation containing a lower dose of a gallium salt to prevent recurrence. In the treatment of loss of calcium from bone due to periodontal disease a gallium salt and a delivery agent may be administered topically in an intra-oral formulation comprising, for example, a highly concentrated rinse, gel, or other pharmaceutically acceptable carrier for the local treatment of periodontal disease.

In one embodiment, the treatment of cancer is provided by administration of an effective amount of the pharmaceutical formulation of the present invention. Effective amounts of gallium include dosage amounts and schedules that, when orally administered, correspond to previously-reported administration schedules via intravenous or subcutaneous injection of gallium salts. For example, in one embodiment the oral equivalent of 700-750 mg/m$^2$ of gallium nitrate administered by short infusion is orally administered every 2-3 weeks, or the oral equivalent of 300 μg/m$^2$/day administered by infusion is administered for three consecutive days, to be repeated every 2 weeks; or the oral equivalent of 300 mg/m$^2$/day administered by infusion for 7 consecutive days is orally administered, to be repeated every 3-5 weeks. See e.g. Foster et al., "Gallium Nitrate: The Second Metal With Clinical Activity", Cancer Treatment Reports, 70:1311:1319 (1986), which is hereby incorporated by reference.

In another embodiment, a topical composition comprising a gallium salt (e.g. gallium nitrate) and a delivery agent are applied to the skin to treat skin conditions including, wrinkles due to aging, and skin defects due to prior injury, such as acne or previous trauma. See U.S. Pat. No. 5,556,645, which is hereby incorporated by reference.

In one embodiment, a topical composition comprising a gallium salt (e.g., gallium nitrate) and a delivery agent of the present invention is applied to treat a wound. In a still further embodiment, topical composition of the present invention is incorporated into or applied to a bandage or dressing for a wound. See U.S. Pat. No. 6,165,514, which is hereby incorporated by reference.

The following example illustrates the invention without limitation. All parts are given by weight unless otherwise indicated.

EXAMPLE 1

The powder blend of gallium nitrate and SNAD at various ratios. There were no color changes in all these powder blends

| Sample | gallium nitrate (g) | SNAD (g) |
|--------|---------------------|----------|
| #1     | 0.5                 | 1        |
| #2     | 1                   | 1        |
| #3     | 0.5                 | 2.5      |

This indicates that dosage forms in the form of un-compressed powders (e.g. powder packets) are not as susceptible to oxidation.

EXAMPLE 2

Component of gallium nitrate and SNAD powder blend that was compressed using a Korsch EK-0 single punch tablet press at 700 psi. The initial powder blend of white turned dark brown immediately after compression

| Ingredients | Weight (g) |
| --- | --- |
| gallium nitrate | 0.5 |
| SNAD Disodium | 1.0 |

EXAMPLE 3

The inclusion of colloidal silica (Aerosil 200)® in the powder blend of Example 2. There were no color changes in the powder blends with Aerosil. 200 mg of the blend was compressed on a Korsch EK-O single punch tablet press at a pressure of 700 psi with no color changes.

| Ingredients | Weight (g) |
| --- | --- |
| gallium nitrate | 0.5 |
| colloidal silica | 0.2 |
| SNAD Disodium | 1.0 |

EXAMPLE 4

Wet granulation of gallium nitrate and SNAD with polyvinyl pyrollidone (PVP) as the granulating fluid. There were no color changes during powder blending and preparation of wet granules.

| Ingredients | Weight (g) |
| --- | --- |
| gallium nitrate | 0.5 |
| SNAD Disodium | 1.0 |
| PVP (1%) | q.s |

Dark coloration was observed in granules after drying in a vacuum oven at 40° C. for 4 hours. This indicates that water released during drying contributed to an oxidation reaction and that the amount of PVP used was not sufficient in this example and under these processing conditions to prevent discoloration.

EXAMPLE 5

The inclusion of microcrystalline cellulose (Ceolus®) in the gallium nitrate and SNAD powder blend of Example 4. The wet granules were dried in a vacuum oven [Model 282A, Fisher Scientific] at 40° C. for 4 hours.

| Ingredients | Weight (g) |
| --- | --- |
| Gallium Nitrate | 0.5 |
| SNAD Disodium | 1.0 |
| microcrystalline cellulose | 0.5 |
| PVP (1%) | q.s |

Dark coloration was observed after drying the granules. The observation indicated that a compression aid such as microcrystalline cellulose is inefficient under these conditions in stabilizing gallium nitrate and SNAD mixture.

EXAMPLE 6

The powder blend of Gallium Nitrate and SNAD with starch. The powder blend was granulated with PVP 1%, and the wet granules were dried in a vacuum oven at 40° C. for 4 hours. There were no color changes during the process of powder blending, wet granulation and drying of wet granules. The formulation demonstrated the utility of using absorbing excipients such as starch to stabilize gallium nitrate/SNAD mixtures.

| Ingredients | Weight (g) |
| --- | --- |
| gallium nitrate | 0.5 |
| SNAD Disodium | 1.0 |
| starch | 1.0 |
| PVP (1%) | q.s |

EXAMPLE 7

The components of a stable gallium nitrate/SNAD formulation. There were no color changes during the process of powder blending, wet granulation and drying of wet granules. PVP was used as the granulating liquid. Tablets (200 mg weight) were compressed using a single punch tablet press at 700 psi. The formulation demonstrated the effectiveness of excipients such as starch and gelatin in gallium nitrate formulations by powder mixing, wet granulation with PVP and drying in a vacuum oven at 40° C. for 4 hours.

| Ingredients | Weight (g) |
| --- | --- |
| gallium nitrate | 0.5 |
| SNAD Disodium | 1.0 |
| starch | 1.0 |
| gelatin | 0.3 |
| PVP (2%) | q.s |

EXAMPLE 8

The components of a stable gallium nitrate/SNAD formulation. There were no color changes during the process of powder blending, wet granulation and drying of wet granules. Gelatin solution, prepared by adding gelatin to purified water at 40° C., was used as the granulating liquid. Dry granules (200 mg) were compressed in a single punch tablet press (Korsch EK-O) at 700 psi. The formulation demonstrated the effectiveness of excipients such as starch, aerosol and gelatin prepared by powder mixing, wet granulation with gelatin solution and drying in a vacuum oven at 40° C. for 4 hours.

| Ingredients | Weight (g) |
| --- | --- |
| gallium nitrate | 0.3 |
| SNAD Disodium | 0.6 |
| starch | 1.0 |
| fumed silica (Aerosil ®) | 0.06 |
| gelatin (10% solution) | q.s |

EXAMPLE 9

The components of a stable gallium nitrate/SNAD formulation. There were no color changes during the process of powder blending, wet granulation and drying of granules. The formulation demonstrated that propyl gallate (an antioxidant) can be included in a gallium nitrate with SNAD formulations.

| Ingredients | Weight (g) |
| --- | --- |
| gallium nitrate | 0.5 |
| SNAD Disodium | 1.0 |
| starch | 1.0 |
| propyl gallate | 0.03 |
| PVP (1% solution) | q.s |

EXAMPLE 10

Formulation of gallium nitrate/SNAD using a combination of starch and fumed silica were prepared. Wet granules were prepared using PVP solution as the granulating solution. Each tablet contains 180 mg of Gallium nitrate nonahydrate (30 mg of Gallium metal per tablet).

| Components | Weight/tablet (mg) |
| --- | --- |
| gallium nitrate | 180 |
| SNAD | 150 |
| pregelatinized starch | 100 |
| fumed silica | 10 |
| croscarmellose sodium | 16 |
| PVP (1%) | q.s |
| croscarmellose sodium (extragranular) | 45 |
| pregelatinized starch (extragranular) | q.s |
| Expected tablet weight | 550 mg |

EXAMPLE 11

Formulation of gallium nitrate/SNAD with sodium citrate and propyl gallate were prepared. A combination of starch and Aerosil was used as the diluent. Wet granules were prepared using PVP solution as the granulating solution. Each tablet contains 180 mg of gallium nitrate nonahydrate (30 mg of Gallium metal per tablet).

| Components | Weight/tablet (mg) |
| --- | --- |
| gallium nitrate | 180 |
| SNAD | 150 |
| pregelatinized Starch | 100 |
| fumed silica | 10 |
| croscarmellose sodium | 12 |
| sodium citrate | 18 |
| propyl gallate | 6 |
| PVP (1%) | q.s |
| croscarmellose sodium (extragranular) | 48 |
| pregelatinized starch (extragranular) | q.s |
| Expected tablet weight | 600 mg |

EXAMPLE 12

Formulation of gallium nitrate/SNAD with an aqueous solution of gallium nitrate used as the granulating solution. The weight ratio of gallium nitrate:SNAD is 1:10. Starch was used as the diluent. Wet granules were prepared using the aqueous solution of gallium nitrate as the granulating solution. Each tablet contains 180 mg of gallium nitrate nonahydrate (30 mg of gallium metal per tablet).

| Components | Weight/tablet (mg) |
| --- | --- |
| Gallium Nitrate (liquid) | 180 |
| SNAD | 150 |
| pregelatinized starch | 150 |
| croscarmellose sodium | 13 |
| sodium citrate | 19 |
| PVP | 0.2 |
| croscarmellose sodium (extragranular) | 36 |
| pregelatinized starch (extragranular) | q.s |
| Expected tablet weight | 600 mg |

EXAMPLE 13

All the ingredients in the table below were screened through a sieve of size #35 (pore size of 500 µm). The required amounts of Aerosil 200 (colloidal silica), pregelatinized starch, sodium citrate and povidone were weighed and blended using a mortar and a pestle for about 5 minutes. An aqueous solution of gallium nitrate was prepared by dissolving 3.6 g of gallium nitrate (amount needed to make 20 tablets) in about 2-3 g of water. When a clear solution of gallium nitrate is obtained, the powder blend of excipients was granulated by adding the aqueous gallium nitrate solution drop wise.

Components of Oral Gallium Nitrate Tablets of Example 13. Each Tablet Contains 180 mg of Gallium Nitrate (30 mg of Gallium Metal)

| Ingredients | mg/tablets |
| --- | --- |
| gallium nitrate | 180 |
| pregelatinized starch | 500 |
| Aerosil 200 | 52 |
| sodium citrate | 21 |
| Povidone K90 | 2 |
| croscarmellose sodium | 37 |
| magnesium sterate | 8 |
| TOTAL | 800 mg |

After addition of each drop of gallium nitrate solution, the powder blend was gently mixed. About 1 g of purified water was added to complete the granulation process. The wet granules were dried in a vacuum oven (Isotemp Model 282A; Fisher Scientific) at 40° C. until the moisture content is about 5%. Dried granules were then milled and screened through a sieve #35 to obtain granules of uniform sizes. The dried granules were analyzed based on the moisture content, and gallium per weight of granules. The dried granules were blended for 5 minutes with the required amount of croscarmellose sodium and magnesium stearate and compressed into a tablet.

EXAMPLE 14

Tablets were prepared as in Example 13, except 300 grams of SNAD replaced 300 grams of pregelatinized starch. The tablets of Example 14 had the amounts shown in the table below.

Components of Oral Gallium Nitrate/SNAD Tablets of Example 14. Each Tablet Contains 180 mg of Gallium Nitrate (30 mg of Gallium Metal)

| Ingredients | mg/tablets |
|---|---|
| Gallium Nitrate | 180 |
| SNAD | 300 |
| Pregelatinized Starch | 200 |
| Aerosil 200 | 52 |
| Sodium citrate | 21 |
| Povidone K90 | 2 |
| Croscarmellose sodium | 37 |
| Magnesium sterate | 8 |
| TOTAL | 800 mg |

The pharmacokinetic profiles of the formulations of Examples 13 and 14 were evaluated in beagles. Beagle studies were conducted in accordance with the approved protocol by the Animal Care and Use Committee of Emisphere Technologies. Each beagle was orally administered the Gallium nitrate tablets of Examples 13 and 14. The dose per beagle is 180 mg of gallium nitrate (or 30 mg of gallium metal). Beagles were fasted at least 8 hrs prior to dosing and were fed immediately after study. Fast not to exceed 24 hrs. Blood samples of about 0.5 ml volume was withdrawn from the jugular vein before and after dosing. The time points for blood withdrawal were: −15, +10, 20, 30, 40, 50 min, 1, 2, 3, 4, 8, 24 hr. The blood samples were put on ice immediately after collection then centrifuged for 10 minutes at 3000 RPM at approximately 4° C. (within 45 minutes of collection). The plasma samples were stored in −20° C. until time of analysis of gallium levels. Plasma gallium metal levels were analyzed by ICP (inductively coupled plasma atomic emission spectroscopy) method. Plasma gallium concentrations (ng/mL) are shown below:

Serum Levels, Mean and Stand Deviation of Beagles Dosed Gallium Formulation of Example 13

| hours | DOG1 | DOG2 | DOG3 | DOG4 | mean | stdev |
|---|---|---|---|---|---|---|
| 0 | 0 | 0 | 0 | 0 | 0 | 0 |
| 10 minutes | 0 | 0 | 0 | 0 | 0 | 0 |
| 20 minutes | 0 | 0 | 0 | 0 | 0 | 0 |
| 30 minutes | 0 | 0 | 0 | 0 | 0 | 0 |
| 40 minutes | 0 | 0 | 0 | 118.8 | 29.7 | 59.4 |
| 50 minutes | 0 | 0 | 0 | 0 | 0 | 0 |
| 1 hour | 0 | 0 | 113.5 | 118.4 | 57.975 | 66.97365 |
| 2 hours | 260.7 | 159.4 | 183.6 | 284.6 | 222.075 | 60.02707 |
| 3 hours | 250.2 | 304.3 | 202 | 300.1 | 264.15 | 48.17209 |
| 4 hours | 273.9 | 377.3 | 199.5 | 341 | 297.925 | 78.35927 |
| 8 hours | 219.4 | 418.2 | 203 | 347 | 296.9 | 103.3556 |
| 24 hours | 0 | 156.2 | 0 | 128.7 | 71.225 | 83.00628 |

Serum Levels, Mean and Stand Deviation of Dogs Dosed Gallium Formulation of Example 14

| Time | DOG1 | DOG2 | DOG3 | DOG4 | mean | stdev |
|---|---|---|---|---|---|---|
| 0 | 0 | 0 | 0 | 0 | 0 | 0 |
| 10 minutes | 0 | 0 | 0 | 0 | 0 | 0 |
| 20 minutes | 0 | 0 | 0 | 0 | 0 | 0 |
| 30 minutes | 0 | 0 | 0 | 0 | 0 | 0 |
| 40 minutes | 173.6 | 0 | 128.2 | 0 | 75.45 | 77.1385 |
| 50 minutes | 197.1 | 143.6 | 207.6 | 0 | 137.075 | 82.77818 |
| 1 hour | 261.6 | 247.6 | 229.2 | 0 | 184.6 | 107.1965 |
| 2 hours | 436.3 | 382.9 | 433.9 | 314.2 | 391.825 | 49.63272 |
| 3 hours | 449.9 | 407.1 | 407.9 | 388.4 | 413.325 | 22.51204 |
| 4 hours | 493 | 386.5 | 534.7 | 386.5 | 450.175 | 65.35952 |
| 8 hours | 449.7 | 389.6 | 504.9 | 481.3 | 456.375 | 43.24173 |
| 24 hours | 138.7 | 126.3 | 310.9 | 193 | 192.225 | 72.9647 |
|  | 0 | 0 | 0 | 0 | 0 | 0 |
|  | 0 | 0 | 0 | 0 | 0 | 0 |

These results are also shown in FIG. 1.

The above mentioned patents, applications, test methods, and publications are hereby incorporated by reference in their entirety.

Many variations of the present invention will suggest themselves to those skilled in the art in light of the above detailed description. All such obvious variations are within the fully intended scope of the appended claims.

What is claimed is:

1. A method of preparing an oral pharmaceutical formulation comprising
   (a) a hydrate of gallium nitrate, and
   (b) at least one delivery agent selected from N-(8-[2-hydroxybenzoyl]-amino) caprylic acid, N-(10-[2-hydroxybenzoyl]-amino) decanoic acid, and pharmaceutically acceptable salts thereof;
   the method comprising at least one of the following steps:
      (a) (i) preparing wet granules consisting essentially of (A) the hydrate of gallium nitrate, (B) the at least one delivery agent; and (C) (i) starch and polyvinylpyrrolidone, (ii) starch, gelatin and polyvinylpyrrolidone, (iii) starch, fumed silica and gelatin, or (iv), starch, propyl gallate and polyvinylpyrrolidone; and
         (ii) drying the wet granules at a temperature between 30° C. and 50° C.; and
      (b) using a low compression pressure of about 700 psi to prepare tablets comprising the at least one delivery agent, colloidal silicon dioxide and the hydrate of gallium nitrate,
   wherein decomposition of the hydrate of gallium nitrate in the oral pharmaceutical formulation is reduced.

2. The method of claim 1, wherein the drying occurs for 2-12 hours.

3. The method of claim 1 wherein the delivery agent is N-(10-[2-hydroxybenzoyl]-amino) decanoic acid, or a pharmaceutically acceptable salt thereof.

4. The method of claim 3 wherein the delivery agent is the disodium salt of N-(10-[2-hydroxybenzoyl]-amino) decanoic acid.

5. The method of claim 1 wherein the delivery agent is N-(8-[2-hydroxybenzoyl]-amino) caprylic acid, or a pharmaceutically acceptable salt thereof.

6. The method of claim 1, wherein said pharmaceutical formulation, upon oral ingestion to a human, provides one or more of the following:
   (a) plasma gallium concentrations of about 0.1 to about 5 μg/ml or about 0.9 to about 2.0 μg/ml,
   (b) average steady state plasma levels of gallium from about 1000 to about 2500 ng/ml, or
   (c) a decrease in serum calcium (corrected for albumin) of at least 2.0 mg/dl in a human with hypercalcemia.

7. The method of claim 1, wherein the method comprises step (a).

8. The method of claim 1, wherein the method comprises step (b).

9. The method of claim 1, wherein the granules consist essentially of the hydrate of gallium nitrate, the at least one delivery agent, starch and polyvinylpyrrolidone.

10. The method of claim 1, wherein the granules consist essentially of the hydrate of gallium nitrate, the at least one delivery agent, starch, gelatin and polyvinylpyrrolidone.

11. The method of claim 1, wherein the granules consist essentially of the hydrate of gallium nitrate, the at least one delivery agent, starch, fumed silica and gelatin.

12. The method of claim 1, wherein the granules are dried at about 40° C.

13. The method of claim 1, wherein discoloration of the pharmaceutical formulation is reduced.

14. The method of claim 1, wherein the decomposition which is reduced is oxidative decomposition.

15. The method of claim 1, wherein the granules consist essentially of the hydrate of gallium nitrate, the at least one delivery agent, starch, propyl gallate, and polyvinylpyrrolidone.

16. The method of claim 1, wherein the hydrate of gallium nitrate is gallium nitrate nonahydrate.

* * * * *